United States Patent
Saji et al.

(10) Patent No.: US 9,238,083 B2
(45) Date of Patent: Jan. 19, 2016

(54) MOLECULAR PROBE FOR IMAGING OF PANCREATIC ISLETS AND USE OF THE SAME

(75) Inventors: Hideo Saji, Kyoto (JP); Nobuya Inagaki, Kyoto (JP); Kentaro Toyoda, Kyoto (JP); Hiroyuki Kimura, Kyoto (JP); Konomu Hirao, Kyoto (JP); Kenji Nagakawa, Kyoto (JP); Hirokazu Matsuda, Kyoto (JP)

(73) Assignees: Kyoto University, Kyoto (JP); ARKRAY, Inc., Kyoto (JP)

( * ) Notice: Subject to any disclaimer, the term of this patent is extended or adjusted under 35 U.S.C. 154(b) by 446 days.

(21) Appl. No.: 12/893,896

(22) Filed: Sep. 29, 2010

(65) Prior Publication Data

US 2011/0081663 A1 Apr. 7, 2011

Related U.S. Application Data

(60) Provisional application No. 61/247,692, filed on Oct. 1, 2009.

(30) Foreign Application Priority Data

Sep. 30, 2009 (JP) .................... 2009-228658

(51) Int. Cl.
*A61K 51/08* (2006.01)
*C07K 14/00* (2006.01)

(52) U.S. Cl.
CPC .................... *A61K 51/08* (2013.01)

(58) Field of Classification Search
None
See application file for complete search history.

(56) References Cited

U.S. PATENT DOCUMENTS 6,821,949 B2 * 11/2004 Bridon et al. ............ 514/5.9
2009/0180953 A1 * 7/2009 Gotthardt et al. ............ 424/1.69

FOREIGN PATENT DOCUMENTS

| EP | 1867634 | 12/2007 |
|---|---|---|
| JP | 09-292466 | 11/1997 |
| JP | 2008-511557 | 4/2008 |
| WO | WO 2004/035744 | 4/2004 |
| WO | WO 2006/107106 | 10/2006 |

OTHER PUBLICATIONS

Runge et al., Biochemistry, 2007, 46(19) pp. 5830-5840.*
Goke et al.,J. Bio. Chem., 1993, 268(26) pp. 19650-19655.*
Wicki et al., Clin.Cancer Res., 2007, 13(12), p. 3696-3705.*
Wicki et al., Clin. Cancer res., 2007, 13(12),p. 3696-3705.*
Wicki et al., Clin. Cancer, Res., 2007, 13(12), 3696-3705.*
Miller et al., AnChem. Int. Ed., 2008, 47, 8998-9033.*
Wu et al., Eur. J. Nucl. Med. Mol. Imaging, 2007, 34(11), 1823-1831.*
Wild et al., J. of Nucl. Med., 2006, 47(12), 2025-2033.*
Arkray, Inc., "Leading research on molecular imaging device for supporting treatment of malignant tumor, etc. / development of method for ultra-early diagnosis of diabetes by noninvasive in-vivo pancreatic islets imaging", Interim report of Heisei 19 (2007) fiscal year, out of Heisei 19 to 20 (2007 to 2008) years (Sep. 19, 2008) (partial (pp. 1, 5) translation provided).
S. Al-Sabah et al., "The positive charge at Lys-288 of the glucagon-like peptide-1 (GLP-1) receptor is important for binding the N-terminus of peptide agonists", FEBS Letters 553: 342-346 (2003).
M. Behe et al., "Are radiolabeled GLP-1 receptor antagonists useful for scintigraphy?", 2009 SNM Annual Meeting, abstract, Oral Presentations No. 327 (May 2009).
M. Brom et al., "$^{68}$Ga-labelled exendin-3, a new agent for the detection of insulinomas with PET", Eur. J. Nucl. Med. Mol. Imaging 37: 1345-1355 (2010).
E. Christ et al., "Glucagon-Like Peptide-1 Receptor Imaging for Localization of Insulinomas", J. Clin. Endocrinol Metab. 94(11): 4398-4405 (Nov. 2009).
R. Göke et al., "Exendin-4 is a High Potency Agonist and Truncated Exendin-(9-39)-amide an Antagonist at the Glucagon-like Peptide 1-(7-36)-amide Receptor of Insulin-secreting β-Cells", J. Biol. Chem. 268(26): 19650-19655 (1993).
M. Gotthardt et al., "Use of the incretin hormone glucagon-like peptide-1 (GLP-1) for the detection of insulinomas: initial experimental results", European Journal of Nuclear Medicine 29(5): 598-606 (May 2002).

(Continued)

*Primary Examiner* — Karlheinz R Skowronek
*Assistant Examiner* — Roy Teller
(74) *Attorney, Agent, or Firm* — Morgan, Lewis & Bockius LLP

(57) ABSTRACT

A molecular probe for imaging of pancreatic islets is provided. The molecular probe includes a polypeptide represented by the following formula (1), or a polypeptide that has a homology with the foregoing polypeptide.

(SEQ ID NO. 1)
Z-HGEGTFTSDLSKQMEEEAVRLFIEWLKNGGPSSGAPPPSX-NH$_2$ (1)

Wherein "X" represents a lysine residue, an amino group of a side chain of the lysine residue being labeled with a group represented by the following chemical formula (I),

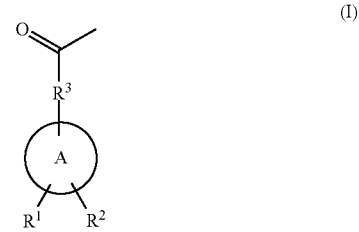

wherein A represents an aromatic hydrocarbon group or an aromatic heterocyclic group; $R^1$ represents a substituent that contains $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, or $^{131}$I; $R^2$ represents either a hydrogen atom, or a substituent different from that represented by $R^1$; and $R^3$ represents any one of a bond, an alkylene group having 1 to 6 carbon atoms, and an oxyalkylene group having 1 to 6 carbon atoms.

15 Claims, 4 Drawing Sheets

(56) References Cited

OTHER PUBLICATIONS

M. Gotthardt et al., "A new technique for in vivo imaging of specific GLP-1 binding sites: First results in small rodents", Regulatory Peptides 137: 162-167 (2006).

B.D. Green et al., "Chronic treatment with exendin(9-39)amide indicates a minor role for endogenous glucagon-like peptide-1 in metabolic abnormalities of obesity-related diabetes in ob/ob mice", J. Endocrinol. 185: 307-317 (2005).

K. Hirao, "Leading research on molecular imaging device for supporting treatment of malignant tumor, etc. / Development of method for ultra-early diagnosis of diabetes by noninvasive in-vivo pancreatic islet imaging", Interim report of Heisei 20 (2008) Fiscal Year, out of Heisei 19 to 20 (2007-2008) years (May 20, 2009) (partial (pp. 1, 2) translation provided).

N. Inagaki, "Research on development of method for ultra-early diagnosis of diabetes by noninvasive in-vivo pancreatic islet imaging", Heisei 19 (2007) Fiscal Year Overview Research Report, Research Project for Medical Equipment Development Promotion, Grants-in-Aid for Scientific Research from Ministry of Health, Labor and Welfare (Apr. 20, 2008) (partial (pp. 1-7, 10-15, 24, 25) translation provided).

N. Inagaki, "Research on development of method for ultra-early diagnosis of diabetes by noninvasive in-vivo pancreatic islet imaging", Heisei 20 (2008) Fiscal Year Overview Research Report, Research Project for Medical Equipment Development Promotion, Grants-in-Aid for Scientific Research from Ministry of Health, Labor and Welfare (Apr. 21, 2009) (partial (pp. 1-7, 10-17, 23, 24) translation provided).

N. Inagaki, "Development of method for ultra-early diagnosis of diabetes by noninvasive in-vivo pancreatic islet imaging", Research of New Medical Devices 13, 72-73 (Mar. 25, 2008) (partial (pp. 72, 73) translation provided).

H. Kimura et al., "Development of in vivo imaging agents targeting glucagon-like peptide-1 receptor (GLP-1R) in pancreatic islets", 2009 SNM Annual Meeting, abstract, Oral Presentations No. 326 (May 2009).

The MICAD Research Team, "[111]In-Diethylenetriaminepentaacetic acid-aminohexanoic acid-Lys[40]-exendin-4".

E. Mukai et al., "Non-invasive imaging of pancreatic islets targeting glucagon-like peptide-1-receptors", 44th EASD Annual Meeting (Rome), abstract, Presentation No. 359 (2008).

E. Mukai et al., "GLP-1 receptor antagonist as a potential probe for pancreatic B-cell imaging", Biophys. Res. Commun. 389(3): 523-526 (2009).

J. W. Neidigh et al., "Exendin-4 and Glucagon-like peptide-1: NMR Structural Comparisons in the Solution and Micelle-Associated States", Biochemistry 40: 13188-13200 (2001).

U. Ritzel et al., "A synthetic glucagon-like peptide-1 analog with improved plasma stability", Journal of Endocrinology 159: 93-102 (1998).

J. Schirra et al., "Exendin(9-39)amide is an Antagonist of Glucagon-like Peptide-1)7-36)amide in Humans", J. Clin. Invest. 101(7): 1421-1430 (Apr. 1998).

G. Vaidyanathan et al., "Protein Radiohalogenation: Observations on the Design of N-Succinimidyl Ester Acylation Agents", Bioconjug. Chem. 1(4), 269-273 (Jul. 1990).

G. Vaidyanathan et al., "Radioiodination of Proteins Using N-Succinimidyl 4-Hydroxy-3-iodobenzoate", Bioconjug. Chem. 4(1), 78-84 (Jan. 1993).

A. Wicki et al., "[Lys[40](Ahx-DTPA-$^{111}$In)NH$_2$]-Exendin-4 is a Highly Efficient Radiotherapeutic for Glucagon-Like Peptide-1 Receptor-Targeted Therapy for Insulinoma", Clin. Cancer Res. 13(12): 3696-3705 (Jun. 15, 2007).

D. Wild et al., "[Lys[40](Ahx-DTPA-$^{111}$In)NH$_2$]Exendin-4, a Very Promising Ligand for Glucagon-like Peptide-1 (GLP-1) Receptor Targeting", J. Nucl. Med. 47: 2025-2033 (2006).

Runge et al., "Crystal Structure of the Ligand-bound Glucagon-like Peptide-1 Receptor Extracellular Domain", Journal of Biological Chemistry, 283:11340-11347 (Apr. 25, 2008).

Wild et al., "Exendin-4-Based Radiopharmaceuticals for Glucagon-like Peptide-1 Receptor PET/CT and SPECT/CT," The Journal of Nuclear Medicine, 51: 1059-1067 (2010).

Mukai et al., "Non-Invasive Imaging of Pancreatic Islets Targeting Glucagon-Like Peptide-1 Receptors," Diabetes, 58 (Supplement 1): 1429-P (2009).

Meng et al., "Influence of Selective Fluorination on the Biological Activity and Proteolytic Stability of Glucagon-like Peptide-1," Journal of Medicinal Chemistry, 51: 7303-7307 (2008).

Wang et al., "Synthesis and evaluation of F-18-exendin as a potential biomarker to measure pancreatic beta-cell mass," Journal of Nuclear Medicine, 51 (Supplement 2): 195 (2010).

Kentaro et al., "Non-Invasive PET Imaging of Pancreatic Islets Targeting Glucagon-Like Peptide-1 Receptors," Diabetes, 59 (Supplement 1): 1631-P (2010).

Extended European Search Report issued in corresponding European Patent Application No. 10820575.8 dated Jun. 12, 2015.

Mukai et al., "Non-Invasive Imaging of Pancreatic Islets Targeting Glucagon-Like Peptide-1 Receptors," Diabetologia, 51 (Supplement 1): 359 (2008).

* cited by examiner transverse view   sagittal view   coronal view

MOLECULAR PROBE FOR IMAGING OF PANCREATIC ISLETS AND USE OF THE SAME

This application claims priority to Provisional Application No. 61/247,692. filed Oct. 1, 2009 and Japanese Application No. JP 2009-228658, filed Sep. 30, 2009, each of which is hereby incorporated by reference in its entirety.

SEQUENCE LISTING SUBMISSION VIA EFS-WEB

A computer readable text file, entitled "068022-5018-SequenceListing.txt," created on or about Sep. 29, 2010 with a file size of about 13 kb contains the sequence listing for this application and is hereby incorporated by reference in its entirety.

TECHNICAL FIELD

The present invention relates to a molecular probe for imaging of pancreatic islets, and the use of the same.

BACKGROUND ART

Today, type-II diabetics are continuously increasing in Japan, and the estimated number of the same exceeds 8,200,000. As a measure against this increase, interventions for preventing diabetes from developing have been made based on the glucose tolerance test, resulting, however, in unsatisfactory effects. The cause is as follows: at such a borderline stage that functional abnormalities are found by the glucose tolerance test, disorders of pancreatic islets have already advanced to a high degree, and this stage possibly is too late as a time for starting interventions.

More specifically, in the diabetes developing process, the amount of pancreatic islets (particularly, the amount of pancreatic β-cells) decreases prior to the occurrence of glucose tolerance abnormalities. Therefore, when functional abnormalities are detected or there are subjective symptoms, diabetes has already reached the stage where it is too difficult to be treated. On the other hand, if a decrease in the amount of pancreatic islets and/or the amount of pancreatic β-cells can be detected at an early stage, there is a possibility for the prevention and treatment of diabetes. Therefore, a technique for noninvasive imaging of pancreatic islets, particularly a technique for noninvasive imaging of pancreatic islets for determining the amount of pancreatic islets and/or the amount of pancreatic β-cells, has been desired for prevention and diagnosis of diabetes. Among these, a molecular probe that enables noninvasive imaging of pancreatic islets, preferably pancreatic β-cells, and noninvasive determination of an amount of pancreatic β-cells has been desired in particular.

In designing a molecular probe for imaging of pancreatic islets, various target molecules in pancreatic cells, particularly functional proteins specific in the β-cells, are being researched. Among these, GLP-1R (glucagon-like peptide-1 receptor) is being researched as a target molecule; GLP-1R is distributed in pancreatic β-cells, and is seven-transmembrane G protein coupled receptor.

As molecular probes for imaging that use GLP-1R as a target molecule, the following are researched: a peptide derivative of GLP-1; a peptide derivative of exendin-3; and a peptide derivative of exendin-4 (e.g., Patent Document 1).

Further, the following, for example, also are researched: a molecular probe obtained by labeling a derivative of exendin-4(9-39) as a GLP-1R antagonist with [$^{18}$F] fluorine (e.g., Non-Patent Document 1); a molecular probe obtained by labeling a derivative of exendin-4 as an GLP-1R agonist with [$^{111}$In] indium via diethylenetriaminepentaacetic acid (DTPA) (e.g., Non-Patent Documents 2 and 3); and a molecular probe obtained by labeling a derivative of exendin-4(9-39) as a GLP-1R antagonist with [$^{111}$In] indium via DTPA (e.g., Non-Patent Document 3).

However, a novel molecular probe for imaging is desired that enables noninvasive three-dimensional imaging of pancreatic islets.

PRIOR ART DOCUMENT

Patent Document

[Patent Document 1] JP 2008-511557 A

Non-Patent Document

[Non-Patent Document 1] H. Kimura et al. Development of in vivo imaging agents targeting glucagons-like peptide-1 receptor (GLP-1R) in pancreatic islets. 2009 SNM Annual Meeting, abstract, Oral Presentations No. 326

[Non-Patent Document 2] M. Gotthardt et al. A new technique for in vivo imaging of specific GLP-1 binding sites: First results in small rodents, Regulatory Peptides 137 (2006) 162-267

[Non-Patent Document 3] M. Beche et al. Are radiolabeled GLP-1 receptor antagonists useful for scintigraphy? 2009 SNM Annual Meeting, abstract, Oral Presentations No. 327

DISCLOSURE OF INVENTION

Problem to be Solved by the Invention

The present invention provides a molecular probe for imaging that enables noninvasive three-dimensional imaging of pancreatic islets.

Means for Solving Problem

The present invention relates to a molecular probe for use in imaging of pancreatic islets, the precursor comprising any one of the following polypeptides:

a polypeptide represented by the following formula (1);

a polypeptide that is obtained by deletion, insertion, or substitution of one to several amino acids with respect to the polypeptide represented by the following formula (1) and that is capable of binding to pancreatic islets; and a polypeptide that has a homology of 80% or higher with the amino acid sequence of the polypeptide represented by the following formula (1) and that is capable of binding to pancreatic islets, wherein (SEQ ID NO. 1)
Z-HGEGTFTSDLSKQMEEEAVRLFIEWLKNGGPSSGAPPPSX-NH$_2$ (1)

"X" represents a lysine residue, an amino group of a side chain of the lysine residue being labeled with a group represented by the following chemical formula (I), "Z—" indicates that an α-amino group at an N-terminus is not modified, or is modified with a modifying group having no electric charge, and "—NH$_2$" indicates that a carboxyl group at a C-terminus is amidated,

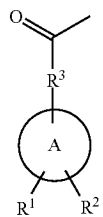

wherein
A represents an aromatic hydrocarbon group or an aromatic heterocyclic group,
R$^1$ represents a substituent that contains $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, or $^{131}$I,
R$^2$ represents either a hydrogen atom, or one or more substituents different from that represented by R$^1$, and
R$^3$ represents any one of a bond, an alkylene group having one to six carbon atoms, and an oxyalkylene group having one to six carbon atoms.

Further, another aspect of the present invention relates to a precursor of a molecular probe for imaging of pancreatic islets, used for producing a molecular probe for imaging of pancreatic islets according to the present invention, the precursor comprising any one of the following polypeptides:
a polypeptide represented by the following formula (2);
a polypeptide that is obtained by deletion, insertion, or substitution of one to several amino acids with respect to the polypeptide represented by the following formula (2) and that is capable of binding to pancreatic islets after being labeled and deprotected; and
a polypeptide that has a homology of 80% or higher with the amino acid sequence of the polypeptide represented by the following formula (2) and that is capable of binding to pancreatic islets after being labeled and deprotected, wherein (SEQ ID NO. 2)
*-HGEGTFTSDLSK*QMEEEAVRLFIEWLK*NGGPSSGAPPPSK-NH$_2$ (2)

"*-" indicates that an α-amino group at an N-terminus is protected by a protecting group, or is modified with a modifying group having no electric charge,
"K*" indicates that an amino group of a side chain of a lysine is protected by a protecting group, and
"—NH$_2$" indicates that a carboxyl group at a C-terminus is amidated.

Effects of the Invention

The present invention enables three-dimensional imaging of pancreatic islets, preferably noninvasive imaging of pancreatic islets, by, for example, positron emission tomography (PET) or single photon emission computed tomography (SPECT).

DESCRIPTION OF THE INVENTION

Figure 1:
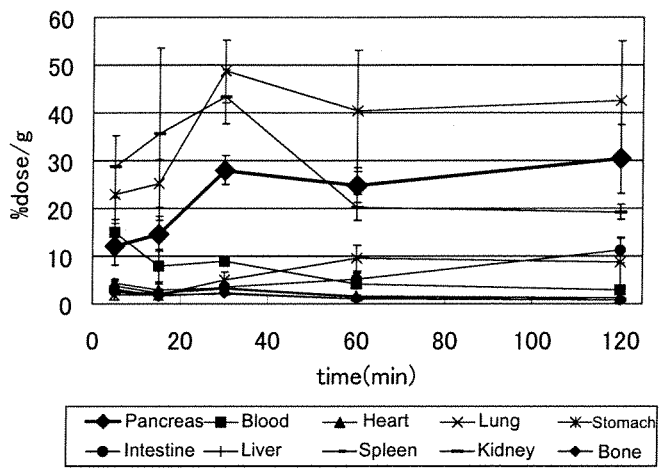
FIG. 1 is an exemplary graph showing variations with time of biodistribution of a molecular probe for imaging according to Example 1.

The diameter of a pancreatic islet is, for example, approximately 50 to 500 μm in the case of a human. In order to noninvasively image or quantify such pancreatic islets in vivo, a molecular probe, for example, is considered to be necessary that can accumulate specifically in pancreatic islets, thereby making contrast between pancreatic islets and surrounding tissues. For this purpose, various researches and developments of molecular probes therefore have been made.

For example, Non-Patent Document 3 reports the research on the affinity of Lys$^{40}$(Ahx-DTPA-$^{111}$In)Exendin-4(9-39), which is a derivative of exendin-4(9-39), with respect to GLP-1R in GLP-1R-positive tumors and pancreatic islet cells. According to this document, the following was proven consequently: the uptake of Lys$^{40}$(Ahx-DTPA-$^{111}$In)Exendin-4 (9-39) in pancreatic islets was about 0.4%, the uptake thereof in the GLP-1R-positive tumor cells was about 7.5%. In other words, the results show that Lys$^{40}$(Ahx-DTPA-$^{111}$In)Exendin-4(9-39) has a low affinity with respect to GLP-1R.

Further, Non-Patent Document 2 reports the results of biodistribution experiments of $^{111}$In-DTPA-Lys$^{40}$-Exendin-4, which is a derivative of exendin-4(1-39), and the SPECT/MRI fusion imaging. The results show that $^{111}$In-DTPA-Lys$^{40}$-Exendin-4 accumulated most in the kidneys and the uptake thereof was about 75% IA/g at 20 hours after the administration, while the uptake of the same in the pancreas was about 5% IA/g at 20 hours after the administration.

However, a novel molecular probe is desired that, for example, is capable of showing specific uptake in the pancreas and causing a desired contrast to be made between the pancreas and the surrounding organs, as compared with the above-described molecular probes.

The present invention was made based on the finding that with use of a molecular probe labeled with a group expressed as the above-described chemical formula (I), it is possible to provide, for example, a molecular probe that exhibits an improved uptake in the pancreas and an improved specificity with respect to the pancreas, and is suitable for the noninvasive three-dimensional imaging of pancreatic islets by PET or SPECT. In other words, the present invention achieves an effect of providing, preferably, a molecular probe suitable for noninvasive three-dimensional imaging of pancreatic islets by PET or SPECT, and more preferably, a molecular probe suitable for noninvasive three-dimensional imaging of pancreatic islets by PET. Further, since the molecular probe of the present invention preferably can show more specific uptake in pancreatic islets as compared with the molecular probes described in the Non-Patent Documents 1, 2, and 3, the present invention achieves an effect of providing a molecular probe suitable for the imaging for quantifying pancreatic islets. The present invention preferably achieves an effect of, for example, more easily synthesizing a molecular probe, as compared with the case of $^{111}$In-DTPA-Lys$^{40}$-Exendin-4 in which DTPA (diethylenetriaminepentaacetic acid) is introduced.

As described above, it is known that in the diabetes developing process, the amount of pancreatic islets decreases prior to the occurrence of glucose tolerance abnormalities. Therefore, by imaging of pancreatic islets and/or determining the amount of pancreatic islets, for example, minute changes in pancreatic islets can be found in a state prior to the development of diabetes or in an initial stage of the same, whereby the ultra-early detection and diagnosis of diabetes are enabled. Thus, the molecular probe for imaging according to the present invention is useful for the prevention, early detection, and diagnosis of diabetes, preferably for the ultra-early detection and diagnosis of diabetes.

Specifically, the present invention relates to the following:

[1] A molecular probe used in imaging of pancreatic islets, the molecular probe comprising any one of the following polypeptides:

a polypeptide represented by the following formula (1);

a polypeptide that is obtained by deletion, insertion, or substitution of one to several amino acids with respect to the polypeptide represented by the following formula (1), and that is capable of binding to pancreatic islets; and a polypeptide that has a homology of 80% or higher with the amino acid sequence of the polypeptide represented by the foregoing formula (1), and that is capable of binding to pancreatic islets, wherein (SEQ ID NO. 1)
Z-HGEGTFTSDLSKQMEEEAVRLFIEWLKNGGPSSGAPPPSX-NH$_2$ (1)

"X" represents a lysine residue, an amino group of a side chain of the lysine residue being labeled with a group represented by the following chemical formula (I), "Z—" indicates that an α-amino group at an N-terminus is not modified, or is modified with a modifying group having no electric charge, and "—NH$_2$" indicates that a carboxyl group at a C-terminus is amidated,

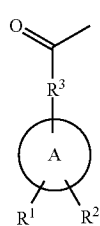

(I)

wherein

A represents an aromatic hydrocarbon group or an aromatic heterocyclic group,

R$^1$ represents a substituent that contains $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, or $^{131}$I, R$^2$ represents either a hydrogen atom, or one or more substituents different from that represented by R$^1$, and R$^3$ represents any one of a bond, an alkylene group having 1 to 6 carbon atoms, and an oxyalkylene group having 1 to 6 carbon atoms.

[2] A precursor of a molecular probe for imaging of pancreatic islets, the precursor being used for producing the molecular probe for imaging of pancreatic islets according to [1], the precursor comprising any one of the following polypeptides:

a polypeptide represented by the following formula (2);

a polypeptide that is obtained by deletion, insertion, or substitution of one to several amino acids with respect to the polypeptide represented by the following formula (2) and that is capable of binding to pancreatic islets after being labeled and deprotected; and a polypeptide that has a homology of 80% or higher with the amino acid sequence of the polypeptide represented by the following formula (2) and that is capable of binding to pancreatic islets after being labeled and deprotected, wherein (SEQ ID NO. 2)
*-HGEGTFTSDLSK*QMEEEAVRLFIEWLK*NGGPSSGAPPPSK-NH$_2$ (2)

"*-" indicates that an α-amino group at an N-terminus is protected by a protecting group, or is modified with a modifying group having no electric charge, "K*" indicates that an amino group of a side chain of a lysine is protected by a protecting group, and "—NH$_2$" indicates that a carboxyl group at a C-terminus is amidated.

[3] A method for producing a molecular probe for imaging of pancreatic islets, the method comprising:

labeling and deprotecting the precursor of a molecular probe for imaging of pancreatic islets according to [2].

[4] The method for producing a molecular probe for imaging of pancreatic islets according to [3], wherein the labeling of the precursor of a molecular probe for imaging of pancreatic islets includes labeling of the precursor using a compound having a group represented by the following chemical formula (I),

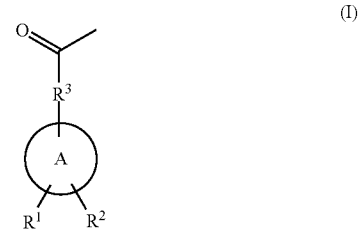

(I)

wherein

A represents an aromatic hydrocarbon group or an aromatic heterocyclic group,

R$^1$ represents a substituent that contains $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, or $^{131}$I, R$^2$ represents either a hydrogen atom, or one or more substituents different from that represented by R$^1$, and R$^3$ represents any one of a bond, an alkylene group having 1 to 6 carbon atoms, and an oxyalkylene group having 1 to 6 carbon atoms.

[5] A kit for imaging of pancreatic islets, the kit comprising at least one of the molecular probe for imaging of pancreatic islets according to [1] and the precursor of a molecular probe for imaging of pancreatic islets according to [2].

[6] The kit according to [5], wherein the molecular probe for imaging of pancreatic islets included in the kit is in a form of a parenteral solution.

[7] A reagent for imaging of pancreatic islets, the reagent comprising the molecular probe for imaging of pancreatic islets according to [1].

[8] A method for imaging pancreatic islets, the method comprising detecting a signal of the molecular probe for imaging of pancreatic islets according to [1], the molecular probe being bound to pancreatic islets preliminarily.

[9] The method for imaging pancreatic islets according to [8], the method further comprising producing the molecular probe for imaging of pancreatic islets according to [1] by labeling and deprotecting the precursor of a molecular probe for imaging of pancreatic islets according to [2].

[10] The method for imaging pancreatic islets according to [8] or [9], the method further comprising determining a state of pancreatic islets on the basis of results of imaging of pancreatic islets using the molecular probe for imaging of pancreatic islets.

[11] A method for determining an amount of pancreatic islets, the method comprising:
detecting a signal of the molecular probe for imaging of pancreatic islets according to [1], the molecular probe being bound to pancreatic islets preliminarily; and
calculating an amount of pancreatic islets from the detected signal of the molecular probe for imaging of pancreatic islets.

[12] The method for determining an amount of pancreatic islets according to [11], further comprising presenting the calculated amount of pancreatic islets.

[Imaging of Pancreatic Islets]

In the present specification, the "imaging of pancreatic islets" refers to molecular imaging of pancreatic islets, and includes the imaging of in-vivo spatial and/or time distribution of pancreatic islets. Further, in the present invention, the imaging of pancreatic islets images preferably pancreatic β-cells as target molecules, and more preferably GLP-1R of pancreatic β-cells as target molecules from the viewpoint of the prevention, treatment, and diagnosis of diabetes. Still further, in the present invention, the imaging of pancreatic islets preferably is noninvasive three-dimensional imaging, from the viewpoint of quantifiability of an amount of pancreatic islets and applicability to humans. The method for imaging is not limited particularly, if it is a method that enables noninvasive imaging of pancreatic islets, and various methods as follows are usable: a method that utilizes positron emission tomography (PET); and a method that utilizes single photon emission computed tomography (SPECT). Among these, PET and SPECT are preferred, from the viewpoint of the quantification of an amount of pancreatic islets using the molecular probe of the present invention.

[Molecular Probe for Imaging of the Present Invention]

The molecular probe for imaging according to the present invention is a molecular probe for imaging of pancreatic islets that comprises a polypeptide used for imaging of pancreatic islets, the polypeptide being represented by the aforementioned formula (1); or preferably a molecular probe for imaging of pancreatic islets that comprises any one of the following polypeptides: a polypeptide represented by the aforementioned formula (1); a polypeptide that is obtained by deletion, insertion, or substitution of one to several amino acid with respect to the polypeptide represented by the foregoing formula (1), and that is capable of binding to pancreatic islets; and a polypeptide that has a homology of 80% or higher with the amino acid sequence of the polypeptide represented by the foregoing formula (1), and that is capable of binding to pancreatic islets.

The amino acid sequence of the polypeptide of the formula (1) is an amino acid sequence according to SEQ ID NO. 1 shown in the Sequence Listing. An amino group of a side chain of a lysine at position 40 in the polypeptide of the formula (1) is labeled with the group represented by the aforementioned chemical formula (I). An α-amino group at an N-terminus of the polypeptide of the formula (1) is either not modified, or modified with a modifying group having no electric charge. A carboxyl group at a C-terminus of the polypeptide of the formula (1) is amidated with an amino group from the viewpoint of improving the affinity between the molecular probe and the pancreatic β-cells, and preferably from the viewpoint of improving the affinity between the molecular probe and GLP-1R of the pancreatic β-cells.

Here, the sequence of the amino acids at positions 1 to 39 in the foregoing formula (1) (SEQ ID NO. 1 in the Sequence Listing) is identical to the amino acid sequence of exendin-4 (1-39) except for a modifying group bondable to an α-amino group at an N-terminus. It is known that exendin-4(1-39) is an analog of GLP-1, and bonds to GLP-1R expressed on the pancreatic β-cells. The molecular probe for imaging according to the present invention also is capable of binding to pancreatic islets, preferably the pancreatic β-cells, and more preferably GLP-1R of the pancreatic β-cells. Thus, the molecular probe for imaging according to the present invention can also be used as a molecular probe for imaging GLP-1R of the pancreatic β-cells.

In the present specification, the description of "being capable of binding to pancreatic islets" means the following: from the viewpoint of the quantifiability of an amount of pancreatic islets and the application of the present invention to the examination and diagnosis, the molecular probe for imaging according to the present invention preferably is capable of binding to the pancreatic β-cells, more preferably is at least specific to the pancreatic β-cells in the pancreas, and further more preferably is at least specific to the pancreatic β-cells to such an extent that a signal thereof has a contrast sufficiently distinguishable from a signal of another organ/tissue in the signal detection in the noninvasive imaging with respect to a human.

Further, in another embodiment of the present invention, the molecular probe for imaging according to the present invention may include a polypeptide used in imaging of pancreatic islets that is obtained by deletion, insertion, or substitution of one to several amino acids with respect to the polypeptide of the foregoing formula (1), and that is capable of binding to pancreatic islets. Here, exemplary ranges expressed by the foregoing description of "one to several" include the following ranges: 1 to 10; 1 to 9; 1 to 8; 1 to 7; 1 to 6; 1 to 5; 1 to 4; 1 to 3; 1 to 2; and 1. In the molecular probe for imaging according to this embodiment of the present invention also, in the case of the polypeptide obtained by deletion, insertion, or substitution of one to several amino acids with respect to the polypeptide of the foregoing formula (1), it is preferable that the polypeptide includes one lysine at a C-terminus to be labeled with a group represented by the aforementioned chemical formula (I), and that a carboxyl group at a C-terminus is amidated. Further, in the molecular probe for imaging according to the present embodiment of the present invention, an α-amino group at an N-terminus may not be modified, or may be modified with a modifying group having no electric charge. The polypeptide obtained by deletion, insertion, or substitution of one to several amino acids with respect to the polypeptide of the foregoing formula (1) preferably has a working effect identical to that of the polypeptide of the formula (1).

In still another embodiment of the present invention, the molecular probe for imaging according to the present invention may include a polypeptide used in imaging of pancreatic islets that has a homology of 80% or higher with the amino acid sequence of the polypeptide of the foregoing formula (1), and that is capable of binding to pancreatic islets. Here, the "homology" may be any value calculated by an algorithm usually used by those skilled in the art, for example, BLAST or FASTA, or alternatively, it may be based on a value obtained by dividing the number of identical amino acid residues existing in two polypeptides compared, by the number of amino acids of an entire length of one of the polypeptides. Exemplary ranges of the homology may include the following ranges: not less than 85%; not less than 90%; and not less than 95%. In the molecular probe for imaging according to this embodiment of the present invention also, in the case of a polypeptide having a homology of 80% or higher with the polypeptide of the foregoing formula (1), it is preferable that the polypeptide includes one lysine at a C-terminus to be labeled with a group represented by the aforementioned chemical formula (I), and that a carboxyl group at a C-terminus is amidated. Further, in the molecular probe for imaging according to the present embodiment of the present invention, an α-amino group at an N-terminus may not be modified, or may be modified with a modifying group having no electric charge. The polypeptide having a homology of 80% or higher with the amino acid sequence of the polypeptide of the foregoing formula (1) preferably has a working effect identical to that of the polypeptide of the formula (1).

The molecular probe for imaging according to the present invention is, as described above, used in imaging of pancreatic islets, preferably in noninvasive imaging of pancreatic islets from the viewpoint of the application of the same to the examination and diagnosis with respect to humans, and also preferably in imaging of pancreatic islets for the quantification of an amount of pancreatic islets from the same viewpoint. Further, the molecular probe for imaging according to the present invention is used preferably in imaging of pancreatic islets for prevention, treatment, or diagnosis of diabetes, and more preferably in imaging of GLP-1R of the pancreatic β cells for prevention, treatment, or diagnosis of diabetes. The imaging of pancreatic islets for these purposes may be carried out by, for example, PET or SPECT. Therefore, the molecular probe for imaging according to the present invention can be used as, for example, a composition, an imaging reagent, a contrast medium or an image diagnostic agent used in imaging as described above.

[Amino Group of Side Chain of Lysine Residue]

In the molecular probe for imaging according to the present invention, the amino group of the side chain of the lysine residue represented by X in the amino acid sequence of the polypeptide of the aforementioned formula (1), that is, the amino group of the side chain of the lysine at position 40 in the polypeptide of the aforementioned formula (1), is labeled with a group represented by the following chemical formula (I):

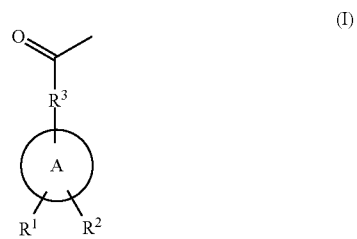

In the foregoing chemical formula (I), A represents an aromatic hydrocarbon group or an aromatic heterocyclic group. The aromatic hydrocarbon group preferably is an aromatic hydrocarbon group having 6 to 18 carbon atoms, and examples of the same include phenyl group, o-tolyl group, m-tolyl group, p-tolyl group, 2,4-xylyl group, p-cumenyl group, mesityl group, 1-naphthyl group, 2-naphthyl group, 1-anthryl group, 2-anthryl group, 9-anthryl group, 1-phenanthryl group, 9-phenanthryl group, 1-acenaphthyl group, 2-azulenyl group, 1-pyrenyl group, 2-triphenylenyl group, o-biphenylyl group, m-biphenylyl group, p-biphenylyl group, and terphenyl group. The aromatic heterocyclic group preferably is a 5 to 10-membered heterocyclic group having one or two of a nitrogen atom, an oxygen atom, or a sulfur atom, and examples of the same include triazolyl group, 3-oxadiazolyl group, 2-furyl group, 3-furyl group, 2-thienyl group, 3-thienyl group, 1-pyrrolyl group, 2-pyrrolyl group, 3-pyrrolyl group, 2-pyridyl group, 3-pyridyl group, 4-pyridyl group, 2-pyradyl group, 2-oxazolyl group, 3-isoxyazolyl group, 2-thiazolyl group, 3-isothiazolyl group, 2-imidazolyl group, 3-pyrazolyl group, 2-quinolyl group, 3-quinolyl group, 4-quinolyl group, 5-quinolyl group, 6-quinolyl group, 7-quinolyl group, 8-quinolyl group, 1-isoquinolyl group, 2-quinoxalynyl group, 2-benzofuryl group, 2-benzothienyl group, N-indolyl group, and N-carbazolyl group. A preferably is, among these, phenyl group, triazolyl group, or pyridyl group, and more preferably, phenyl group.

In the aforementioned chemical formula (I), $R^1$ represents a substituent that contains $^{11}C$, $^{13}N$, $^{15}O$, $^{18}F$, $^{64}Cu$, $^{67}Ga$, $^{68}Ga$, $^{75}Br$, $^{76}Br$, $^{77}Br$, $^{99m}Tc$, $^{111}In$, $^{123}I$, $^{124}I$, $^{125}I$, or $^{131}I$ (hereinafter also referred to as a "radioactive-nuclide-containing substituent"). Examples of the "radioactive-nuclide-containing substituent" in the present specification include radioactive nuclides such as $^{11}C$, $^{13}N$, $^{15}O$, $^{18}F$, $^{64}Cu$, $^{67}Ga$, $^{68}Ga$, $^{75}Br$, $^{76}Br$, $^{77}Br$, $^{99m}Tc$, $^{111}In$, $^{123}I$, $^{124}I$, $^{125}I$, and $^{131}I$; radioactive-nuclide-substituted $C_1$-$C_3$ alkyl groups in which a hydrogen atom is substituted with the aforementioned radioactive nuclide; and radioactive-nuclide-substituted $C_1$-$C_3$ alkoxy groups in which a hydrogen atom is substituted with the aforementioned radioactive nuclide. In the present specification, the "$C_1$-$C_3$ alkyl group" refers to an alkyl group that has 1 to 3 carbon atoms, and examples of the same include methyl group, ethyl group, and propyl group. In the present specification, the "radioactive-nuclide-substituted $C_1$-$C_3$ alkyl group" refers to an alkyl group that has 1 to 3 carbon atoms and in which a hydrogen atom is substituted with the aforementioned radioactive nuclide. In the present specification, the "$C_1$-$C_3$ alkoxy group" refers to an alkoxy group that has 1 to 3 carbon atoms, and examples of the same include methoxy group, ethoxy group, and propoxy group. In the present specification, the "radioactive-nuclide-substituted $C_1$-$C_3$ alkoxy group" refers to an alkoxy group that has 1 to 3 carbon atoms and in which a hydrogen atom is substituted with the aforementioned radioactive nuclide. Among these, $R^1$ preferably is a substituent containing a radioactive halogen, that is, for example, a substituent containing $^{18}$F, $^{75}$Br, $^{76}$Br, $^{77}$Br, $^{123}$I, $^{124}$I, $^{125}$I, or $^{131}$I. From the viewpoint of performing PET, $R^1$ preferably is a substituent containing a radioactive nuclide that emits positron, that is, for example, a substituent containing $^{18}$F, $^{75}$Br, $^{76}$Br, or $^{124}$I. From the viewpoint of performing SPECT, $R^1$ preferably is a substituent containing a radioactive nuclide that emits γ-rays, that is, for example, a substituent containing $^{77}$Br, $^{123}$I, or $^{125}$I. In $R^1$, preferably a hydrogen atom at any one of an ortho-position, a meta-position, and a para-position is substituted with a radioactive nuclide, from the viewpoint of quantification, and more preferably, at a meta-position or a para-position.

In the aforementioned chemical formula (I), $R^2$ represents a hydrogen atom or one or more substituents different from that represented by $R^1$. $R^2$ may be a hydrogen atom or a substituent, but preferably, it is a hydrogen atom. In other words, in the aforementioned chemical formula (I), A preferably does not have a substituent other than $R^1$. In the case where $R^2$ represents a plurality of substituents, these substituents may be identical or different. Examples of the substituent include hydroxyl group, electron attractive groups, electron donative groups, $C_1$-$C_6$ alkyl groups, $C_2$-$C_6$ alkenyl groups, and $C_2$-$C_6$ alkynyl groups. Examples of the electron attractive group include cyano group, nitro group, halogen atoms, carbonyl group, sulfonyl group, acetyl group, and phenyl group. Examples of the halogen atom include fluorine atom, chlorine atom, bromine atom, and iodine atom. In the present specification, the "$C_1$-$C_6$ alkyl group" refers to an alkyl group having 1 to 6 carbon atoms, and examples of the same include methyl group, ethyl group, propyl group, isopropyl group, butyl group, isobutyl group, sec-butyl group, tert-butyl group, pentyl group, isopentyl group, and hexyl group. In the present specification, the "$C_2$-$C_6$ alkenyl group" refers to an alkenyl group having 2 to 6 carbon atoms, and examples of the same include vinyl group, 1-propenyl group, 2-propenyl group, isopropenyl group, 1-butenyl group, 2-butenyl group, and 3-butenyl group. In the present specification, the "$C_2$-$C_6$ alkynyl group" refers to an alkynyl group having 2 to 6 carbon atoms, and examples of the same include ethynyl group, 1-propynyl group, 2-propynyl group, 1-butynyl group, 2-butynyl group, and 3-butynyl group. Among these, the substituent preferably is a hydroxyl group or an electron attractive group.

In the aforementioned chemical formula (I), $R^3$ preferably is a bond, a $C_1$-$C_6$ alkenyl group, or a $C_1$-$C_6$ oxyalkylene group. In the present specification, the "$C_1$-$C_6$ alkenyl group" refers to an alkylene group having 1 to 6 carbon atoms, and examples of the same include straight-chain or branched-chain alkylene groups such as methylene group, ethylene group, propylene group, butylene group, pentyl group, and hexyl group. In the present specification, the "$C_1$-$C_6$ oxyalkylene group" refers to an oxyalkylene group having 1 to 6 carbon atoms, and examples of the same include oxymethylene group, oxyethylene group, oxypropylene group, oxybutylene group, and oxypentyl group. $R^3$ preferably is a bond, methylene group, or ethylene group, and more preferably, a bond, from the viewpoint of the affinity between the molecular probe and pancreatic islets, preferably the affinity between the molecular probe and pancreatic β-cells and more preferably the affinity between the molecular probe and GLP-1R of the pancreatic β-cells.

In the molecular probe for imaging according to the present invention, the group represented by the aforementioned chemical formula (I) preferably is a group represented by the following chemical formula (Ia), and more preferably a group represented by the following chemical formula (Ib) ([$^{18}$F]4-fluorobenzoyl group), a group, represented by the following chemical formula (Ic) ([$^{123}$I]3-iodobenzoyl group), a group represented by the following chemical formula (Id) ([$^{124}$I]3-iodobenzoyl group), a group represented by the following chemical formula (Ie) ([$^{125}$I]3-iodobenzoyl group), and a group represented by the following chemical formula (If) ([$^{131}$I]3-iodobenzoyl group). In the chemical formula (Ia), $R^1$ is as described above.

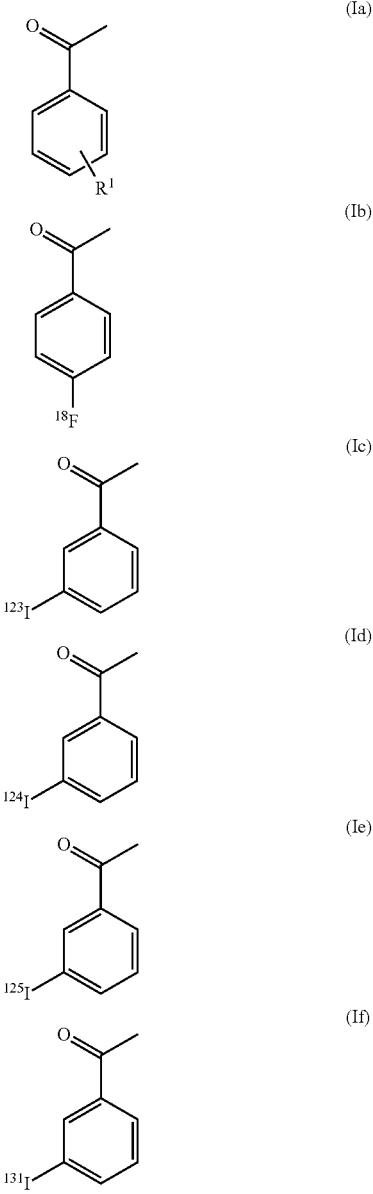

[Modifying Group]

In the molecular probe for imaging according to the present invention, an α-amino group at an N-terminus in the polypeptide of the above-described formula (1) may be modified with a modifying group having no electric charge, from the viewpoint of canceling a positive charge of the α-amino group at the N-terminus thereby suppressing accumulation in kidneys of the molecular probe for imaging according to the present invention. Examples of such a modifying group having no electric charge include 9-fluorenylmethyloxycarbonyl group (Fmoc), tert-butoxycarbonyl group (Boc), benzyloxycarbonyl group (Cbz), 2,2,2-trichloroethoxycarbonyl group (Troc), and allyloxycarbonyl group (Alloc), 4-methoxytrityl group (Mmt), amino group, alkyl groups having 3 to 20 carbon atoms, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy2,3,6-trimethyl-benzenesulfonyl group (Mtr), mesitylene-2-sulfonyl group (Mts), 4,4-dimethoxybenzohydryl group (Mbh), tosyl group (Tos), 2,2,5,7,8-pentamethylchroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene)ethyl group (Dde), 2,6-dichlorobenzyl group (2,6-DiCl-Bzl), 2-chlorobenzyloxycarbonyl group (2-Cl—Z), 2-bromobenzyloxycarbonyl group (2-Br—Z), benzyloxymethyl group (Bom), cyclohexyloxy group (cHxO), t-butoxymethyl group (Bum), t-butoxy group (tBuO), t-butyl group (tBu), acetyl group (Ac), trifluoroacetyl group (TFA), o-bromobenzyloxycarbonyl group, t-butyldimethylsilyl group, 2-chlorobenzyl (Cl-z) group, cyclohexyl group, cyclopentyl group, isopropyl group, pivalyl group, tetrahydropyran-2-yl group, and trimethylsilyl group. Among these, preferably, the modifying group is acetyl group, benzyl group, benzyloxymethyl group, o-bromobenzyloxycarbonyl group, t-butyl group, t-butyldimethylsilyl group, 2-chlorobenzyl group, 2,6-dichlorobenzyl group, cyclohexyl group, cyclopentyl group, isopropyl group, pivalyl group, tetrahydropyran-2-yl group, tosyl group, trimethylsilyl group, or trityl group. More preferably, the modifying group is acetyl group.

[Precursor of Molecular Probe for Imaging According to the Present Invention]

Another aspect of the present invention relates to a precursor of a molecular probe (hereinafter referred to as molecular probe precursor) for imaging, for use in production of the molecular probe for imaging according to the present invention, wherein the precursor contains any one of the following polypeptides: a polypeptide represented by the following formula (2); a polypeptide that is obtained by deletion, insertion, or substitution of one to several amino acids with respect to the polypeptide represented by the following formula (2) and that is capable of binding to pancreatic islets after being labeled and deprotected; and a polypeptide that has a homology of 80% or higher with the amino acid sequence of the polypeptide represented by the following formula (2) and that is capable of binding to pancreatic islets after being labeled and deprotected. The molecular probe for imaging according to the present invention can be prepared using, for example, the precursor of the molecular probe for imaging according to the present invention.

(SEQ ID NO 2)
*-HGEGTFTSDLSK*QMEEEAVRLFIEWLK*NGGPSSGAPPPSK-NH$_2$ (2)

The molecular probe precursor of the present invention is a precursor of a molecular probe for imaging, for use in production of the molecular probe for imaging according to the present invention, wherein the precursor contains the polypeptide of the above-described formula (2), and preferably comprises any one of the following polypeptides: a polypeptide of the foregoing formula (2); a polypeptide that is obtained by deletion, insertion, or substitution of one to several amino acids with respect to a polypeptide of the foregoing formula (2) and that is capable of binding to pancreatic islets after being labeled and deprotected; and a polypeptide that has a homology of 80% or higher with the amino acid sequence of the polypeptide of the foregoing formula (2) and that is capable of binding to pancreatic islets after being labeled and deprotected.

The amino acid sequence of the polypeptide of the aforementioned formula (2) is the amino acid sequence according to SEQ ID NO. 2 shown in the Sequence Listing. A protecting group is bonded to each of an amino group of a side chain of a lysine at position 12 and an amino group of a side chain of a lysine at position 27 of the polypeptide of the foregoing formula (2), in order to protect these amino groups. As to an α-amino group at an N-terminus of the polypeptide of the foregoing formula (2), either a protective group is bonded thereto for protecting the amino group, or the α-amino group is modified with a modifying group having no electric charge. A carboxyl group at a C-terminus of the polypeptide represented by the foregoing formula (2) is amidated by an amino group from the viewpoint of improving the affinity to the pancreatic β-cells. It should be noted that in the molecular probe precursor of the present invention, a protective group or another modifying group may or may not be bonded to the amidated carboxyl group at the C-terminus in the polypeptide of the formula (2), and preferably, none of such groups is bonded thereto. This, however, does not mean that such a configuration in which the amidated carboxyl group is protected by a protecting group or a modified with a modifying group is excluded from the present invention.

When the molecular probe precursor of the present invention that contains the polypeptide of the foregoing formula (2) is labeled with a labeling system for labeling an amino group that will be described later, an amino group of a side chain of a lysine at the C-terminus that is not protected by a protecting group, that is, the amino group of the side chain of the lysine at position 40 in the polypeptide of the formula (2), can be labeled.

Here, the sequence of the amino acids at positions 1 to 39 in the amino acid sequence of the foregoing formula (2) (SEQ ID NO. 2 in the Sequence Listing) is identical to the amino acid sequence of exendin-4(1-39) except for the protective group bonded to the amino group of the side chain of the lysine and the protective group or the modifying group bonded to the α-amino group at the N-terminus.

Further, in another embodiment of the present invention, the molecular probe precursor of the present invention may contain a polypeptide used in imaging of pancreatic islets that is obtained by deletion, insertion, or substitution of one to several amino acids with respect to the polypeptide of the foregoing formula (2), and that is capable of binding to pancreatic islets after being labeled and deprotected. Here, exemplary ranges expressed by the foregoing description of "one to several" are as described above. In the molecular probe precursor according to this embodiment of the present invention also, in the case of a polypeptide obtained by deletion, insertion, or substitution of one to several amino acids with respect to the polypeptide of the foregoing formula (2), it is preferable that one lysine at a C-terminus that can be labeled is included, and that a carboxyl group at a C-terminus is amidated; and in the case where another lysine also is included, an amino group of a side chain of the another lysine preferably is protected by a protecting group. Further, in the molecular probe precursor of according to this embodiment of the present invention, the α-amino group at the N-terminus may not be modified, or may be modified with a modifying group having no electric charge. The polypeptide obtained by deletion, insertion, or substitution of one to several amino acids with respect to the polypeptide of the foregoing formula (2), when being labeled and deprotected, preferably has a working effect identical to that of the polypeptide obtained by labeling and deprotecting the polypeptide of the foregoing formula (2), and more preferably, has a working effect identical to that of the polypeptide of the foregoing formula (1).

Further, in another embodiment of the present invention, the molecular probe precursor of the present invention may contain a polypeptide used in imaging of pancreatic islets that has a homology of 80% or higher with the amino acid sequence of the polypeptide of the foregoing formula (2), and that is capable of binding to pancreatic islets after being labeled and deprotected. Here, what is meant by the "homology" is as described above. In the molecular probe precursor according to this embodiment of the present invention also, in the case of a polypeptide having a homology of 80% or higher with the polypeptide of the foregoing formula (2), it is preferable that one lysine at a C-terminus that can be labeled is included, and that a carboxyl group at a C-terminus is amidated; and in the case where another lysine also is included, an amino group of a side chain of the another lysine preferably is protected by a protecting group. Further, in the molecular probe precursor according to this embodiment of the present invention, the α-amino group at the N-terminus may not be modified, or may be modified with a modifying group having no electric charge. The polypeptide having a homology of 80% or higher with the amino acid sequence of the polypeptide of the foregoing formula (2) preferably has a working effect identical to that of the polypeptide obtained by labeling and deprotecting the polypeptide of the foregoing formula (2), and more preferably, has a working effect identical to that of the polypeptide of the formula (1).

In the foregoing formula (2), "*-" indicates that an α-amino group at an N-terminus is either protected by a protecting group, or is modified with a modifying group having no electric charge. In the foregoing formula (2), "K*" indicates that an amino group of a side chain of a lysine is protected by a protecting group. The modifying group is as described above.

[Protecting Group]

The protecting group is intended to protect the other amino group of the molecular probe precursor than an amino group of a side chain of a lysine at a C-terminus while the latter amino group is being labeled. As the protecting group, any known protecting group capable of performing such a function can be used. The protecting group is not limited particularly, and examples of the same include 9-fluorenylmethyloxycarbonyl group (Fmoc), tert-butoxycarbonyl group (Boc), benzyloxycarbonyl group (Cbz), 2,2,2-trichloroethoxycarbonyl group (Troc), and allyloxycarbonyl group (Alloc), 4-methoxitrityl group (Mmt), amino group, alkyl groups having 3 to 20 carbon atoms, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy2,3,6-trimethyl-benzenesulfonyl group (Mtr), mesitylene-2-sulfonyl group (Mts), 4,4-dimethoxybenzohydryl group (Mbh), tosyl group (Tos), 2,2,5,7,8-pentamethylchroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene)ethyl group (Dde), 2,6-dichlorobenzyl group (2,6-DiCl-Bzl), 2-chlorobenzyloxycarbonyl group (2-Cl—Z), 2-bromobenzyloxycarbonyl group (2-Br—Z), benzyloxymethyl group (Bom), cyclohexyloxy group (cHxO), t-butoxymethyl group (Bum), t-butoxy group (tBuO), t-butyl group (tBu), acetyl group (Ac), and trifluoroacetyl group (TFA). From the viewpoint of handleability, Fmoc or Boc is preferred.

[Method for Producing Molecular Probe for Imaging According to the Present Invention]

The molecular probe for imaging according to the present invention can be produced by labeling and deprotecting the molecular probe precursor containing the polypeptide represented by the foregoing formula (2). By the labeling operation, an amino group of a side chain of a lysine to which no protecting group is bonded, i.e., an amino group of a side chain of a lysine at a C-terminus, can be labeled.

As to the labeling, the molecular probe precursor of the present invention is labeled in a manner suitable for the method for imaging, and thereafter, it is deprotected by removing a protecting group, whereby the preparation is performed. As to the synthesis of the molecular probe precursor, the molecular probe precursor of the present invention can be produced by peptide synthesis in accordance with a typical method such as the Fmoc method, and the peptide synthesis method is not limited particularly.

Exemplary radioactive nuclides used in labeling include $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, and $^{131}$I. Exemplary labeling procedures are as follows: when PET is performed, a positron emission nuclide such as $^{11}$C, $^{15}$O, $^{18}$F, or $^{124}$I is labeled by a known method; and when SPECT is performed, a γ-ray emission nuclide such as $^{99m}$Tc, $^{111}$In, $^{123}$I, or $^{125}$I is labeled by a known method.

The labeling preferably is performed, for example, using a labeling compound having a group represented by the foregoing chemical formula (I). The labeling compound used in the labeling preferably is a succinimidyl ester compound in which the group represented by the foregoing chemical formula (I) is bonded with succinimide via ester bond, more preferably, a succinimidyl ester compound represented by the chemical formula (II) shown below and further more preferably, a succinimidyl ester compound represented by the chemical formula (IIa) shown below. In the chemical formula (II) below, A, $R^1$, $R^2$, and $R^3$ represent the same as those in the case of the foregoing chemical formula (I). In the chemical formula (IIa) below, $R^1$ represents the same as that in the case of the foregoing chemical formula (I).

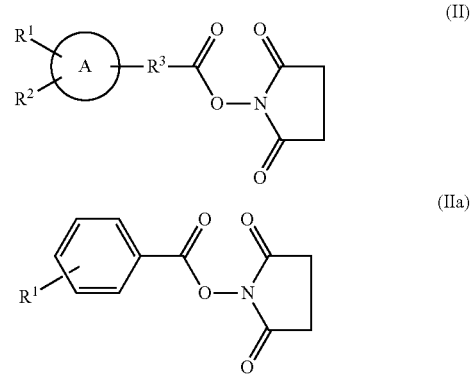

A labeling compound used in the labeling preferably in particular is [$^{18}$F]N-succinimidyl 4-fluorobenzoate, in which $R^1$ in the foregoing chemical formula (IIa) is [$^{18}$F]fluorine atom. When a radioactive nuclide used in the labeling is $^{123}$I, $^{124}$I, $^{125}$I or $^{131}$I, a labeling compound used in the labeling is preferably, for example, [$^{123}$I]N-succinimidyl 3-iodobenzoate, in which $R^1$ in the foregoing formula (IIa) is [$^{123}$I] iodo atom, [$^{124}$I]N-succinimidyl 3-iodobenzoate, in which $R^1$ in the formula (IIa) is [$^{124}$I] iodo atom, [$^{125}$I]N-succinimidyl 3-iodobenzoate, in which $R^1$ in the formula (IIa) is [$^{125}$I] iodo atom, or [$^{131}$I]N-succinimidyl 3-iodobenzoate, in which $R^1$ in the formula (IIa) is [$^{131}$I] iodo atom.

In the method for producing the molecular probe for imaging according to the present invention, the synthesis of the labeling compound having the group represented by the chemical formula (I) may be carried out by an automatic synthesizing device. Alternatively, the synthesis of the labeling compound having the group represented by the foregoing chemical formula (I) and the labeling and deprotecting of a precursor of a molecular probe for imaging in which the foregoing labeling compound is used may be carried out by a single automatic synthesizing device.

Another aspect of the present invention relates to a method for producing the molecular probe for imaging, including: synthesizing polypeptide having an amino acid sequence represented by the following formula (14) using a protecting amino acid in which an α-amino group at an N-terminus and/or a functional group of a side chain is protected by a protecting group; deprotecting amino groups of side chains of lysine at positions 12 (Lys 12) and lysine at positions 27 (Lys 27) in the synthesized polypeptide and reprotecting the deprotected amino groups by protecting groups different from those removed upon the deprotection; deprotecting an amino group of a side chain of lysine at position 40 (Lys 40) in the reprotected polypeptide; radioactively labeling the deprotected amino group of the side chain of Lys 40; and deprotecting the radioactively labeled polypeptide.

```
                                              (SEQ ID NO. 14)
HGEGTFTSDLSKQMEEEAVRLFIEWLKNGGPSSGAPPPSK (14)
```

With this method for producing the molecular probe for imaging, it is possible to selectively label only the amino group of the side chain of Lys 40 as a target. Therefore, with this method for producing the molecular probe for imaging, it is possible to improve the labeling efficiency and also to increase the yield of the radioactively labeled peptide as desired.

The peptide synthesis can be carried out by, for example, a known organic-chemical peptide synthesis method, and the peptide synthesis can be performed according to the descriptions in, for example, the Japanese Biochemical Society (eds.) "*Seikagaku Jikken Koza* (Lecture on Biochemical Experiment)", Vol. 1 "Protein IV" pp. 207 to 495, (1977, Tokyo Kagaku Dojin) and the Japanese Biochemical Society (eds.) "*Shin-Seikagaku Jikken Koza* (New Lecture on Biochemical Experiment)", Vol. 1 "Protein IV" pp. 3 to 74 (1992, Tokyo Kagaku Dojin).

Examples of organic-chemical peptide synthesis methods include the peptide solid-phase synthesis method, and the peptide liquid-phase synthesis method, among which the peptide solid-phase synthesis method is preferred. In the present specification, the "peptide solid-phase synthesis method" refers to a method in which a C-terminus of an amino acid or a peptide is fixed to a solid-phase carrier via a linker, and amino acids are extended one by one toward an N-terminus. Examples of the peptide solid-phase synthesis method include the Fmoc method and the Boc method, among which the Fmoc method is preferred. In the present specification, the "Fmoc method" refers to a method wherein amino acids in which the α-amino group at the N-terminus is protected by Fmoc (9-fluorenylmethyloxycarbonyl group) are used, and they are condensed, so as to synthesize a peptide. More specifically, an amino acid corresponding to a C-terminus of a peptide to be synthesized, or a peptide including an amino acid corresponding to the C-terminus of a peptide to be synthesized, is bonded to a solid-phase carrier such as a resin, the deprotection of an α-amino group at a N-terminus by removing the Fmoc group as a protecting group for an α-amino group at a N-terminus and the washing, and the condensation of the protected amino acids and the washing, are carried out repeatedly, whereby a peptide chain is extended. In the end, a final deprotection reaction is caused, whereby an intended peptide can be synthesized. For example, an automatic peptide synthesizing device may be used in the peptide synthesis. Examples of the automatic peptide synthesizing device include the A443A type (produced by Applied Biosystems), and PSSM8 (produced by Shimadzu Corporation).

When carrying out the peptide synthesis by the Fmoc method, an Fmoc-amino acid derivative used in a conventional Fmoc-peptide synthesis method can be used as a protecting amino acid used in the peptide synthesis. Specifically, for an amino acid (His, Asp, Ser, Lys, Gln, Glu, Arg, Asn, Trp) with a functional group on a side chain, it is possible to use any amino acid in which a functional group is protected by a protecting group depending on the type of the functional group and an α-amino group at a N-terminus is protected by Fmoc. And for other amino acids, it is possible to use any amino acid in which an α-amino group at a N-terminus is protected by Fmoc.

As Lys 12 and Lys 27 that are not to be radioactively labeled, from the viewpoint of selective deprotection, it is preferable to use lysine in which an amino group of its side chain is protected by a protecting group different from that for the amino group of the side chain of Lys 40 to be radioactively labeled. For example, lysine in which an amino group of its side chain is protected by a carbamate-type protecting group other than Fmoc may be used as Lys 40, and lysine in which an amino group of its side chain is protected by a trityl-type protecting group may be used as Lys 12 and Lys 27. Examples of carbamate-type protecting groups other than Fmoc include Boc, Cbz, Alloc and Troc, among which Boc is preferred. Examples of trityl-type protecting groups include Mmt, Trt, Mtt and Mtr. From the viewpoint of more selective deprotection, Mmt and Mtt are preferred.

Next, the amino groups of the side chains of Lys 12 and Lys 27 in the polypeptide of the aforementioned formula (14) are deprotected and reprotected.

It is preferable to deprotect the amino groups, for example, without deprotecting the amino group of the side chain of Lys 40. It is more preferable to selectively deprotect only the amino groups of the side chains of the Lys 12 and Lys 27 without deprotecting the functional groups other than the amino groups of the side chains of Lys 12 and Lys 27. In the case where the protecting groups for the amino groups of the side chains of Lys 12 and Lys 27 are of a trityl-type, for example, they can be removed under weak acid conditions to selectively deprotect the amino groups of Lys 12 and Lys 27. A reagent making the weak acid conditions is, for example, a reagent containing trifluoroacetic acid.

The reprotection includes, for example, protecting the amino groups of Lys 12 and Lys 27 by protecting groups different from those removed, preferably protecting the amino groups by the protecting group for the α-amino group at the N-terminus used in the peptide synthesis, and more preferably protecting the amino groups by Fmoc. For example, Fmoc can be introduced by reacting an Fmoc reagent with the amino groups of the side chains of Lys 12 and Lys 27 in the presence of amine. Examples of the Fmoc reagent include N-(9-fluorenylmethoxy carbonyloxy) succinimide (Fmoc-Osu) and 9-fluorenyl carbonyl chloride (Fmoc-Cl).

Further, when deprotecting and reprotecting the amino groups of the side chains of Lys 12 and Lys 27, the α-amino group at the N-terminus of the polypeptide may also be deprotected and reprotected, for example.

Then, the amino group of the side chain of Lys 40 in the polypeptide of the aforementioned formula (14) is deprotected. As a result, the probe precursor to be radioactively labeled can be obtained.

With regard to the deprotection, at least the amino group of the side chain of Lys 40 needs to be deprotected. Further, from the viewpoint of simplifying the deprotecting operation after the radioactive labeling, the α-amino group at the N-terminus and the functional groups other than the amino groups of the side chains of Lys 12 and Lys 27 are preferably deprotected. Consequently, it is possible to obtain peptide in which the α-amino group at the N-terminus, the amino groups of the side chains of Lys 12 and Lys 27 are protected by protecting groups and the amino group of the side chain of Lys 40 is deprotected. The deprotection can be conducted by a known method depending on the type of the protecting group to be removed. This deprotection may be carried out upon the excision of the peptide from a solid-phase carrier, and for example, the above-described deprotection by removing the protecting group may be carried out under the condition for the excision of the peptide.

Thereafter, the deprotected amino group of the side chain of Lys 40 is radioactively labeled. Since the polypeptide (molecular probe precursor) to be radioactively labeled is in a state where the amino group of the side chain of Lys 40 is deprotected and the amino groups of the side chains of Lys 12 and Lys 27 are protected, and preferably the amino group of the side chain of Lys 40 is deprotected and the amino groups of the side chains of Lys 12 and Lys 27 and the α-amino group at the N-terminus of the polypeptide are protected, it is possible to selectively radioactively-label only the intended amino group of the side chain of Lys 40.

The radioactive labeling can be conducted in accordance with a known method depending on the type of the peptide to be radioactively labeled. Though the labeling compound used in the radioactive labeling is not limited particularly, it may be, for example, the labeling compound having a group represented by the chemical formula (I), or a chelate compound chelatable to a metal radioactive isotope (metal nuclide). Examples of the metal nuclide include $^{64}$Cu, $^{67}$Ga, $^{68}$Ga, $^{82}$Rb, $^{99m}$Tc, $^{111}$In, and $^{186}$Re. Examples of the chelate compound include diethylenetriaminepentaacetic acid (DTPA), 6-hydrazinoeulysin-3-carboxylic acid (HYNIC), tetraazacyclododecanetetraacetic acid (DOTA), dithisosemicarbazone (DTS), diaminedithiol (DADT), mercaptoacetylglycylglycylglycine (MAG3), monoamidemonoaminedithiol (MAMA), diamidedithiol (DADS), and propylene diamine dioxime (PnAO). From the viewpoint of production of the molecular probe for imaging according to the present invention, the labeling compound is preferably the labeling compound having a group represented by the chemical formula (I), more preferably, the succinimidyl ester compound represented by the chemical formula (II), and still more preferably, a succinimidyl ester compound represented by the chemical formula (IIa).

Finally, the remaining protecting groups of the thus radioactively labeled polypeptide are removed. For example, the remaining protecting groups include the protecting groups for the amino groups of the side chains of Lys 12 and Lys 27 and the protecting group for the α-amino group at the N-terminus of the polypeptide. As a result, polypeptide in which the amino group of the side chain of Lys 40 is radioactively labeled can be produced. The deprotection can be conducted in accordance with a known method depending on the type of the protecting groups. In the case where the protecting groups are Fmoc, the deprotection can be carried out, for example, under the piperidine conditions.

From the viewpoint for the production of radioactively-labeled peptide with a high purity, the method for producing the molecular probe for imaging of the present invention may further include a purification step. The purification step can be carried out, for example, between the steps of deprotecting the amino group of the side chain of Lys 40 and radioactively labeling, between the step of radioactively labeling and the subsequent step of deprotecting (final deprotection) and after the final deprotection. Further, the method for producing the molecular probe for imaging of the present invention may include a step of modifying the α-amino group at the N-terminus in the radioactively labeled polypeptide with a modifying group having no electric charge, or a step of amidating the carboxyl group at the C-terminus.

[Method for Imaging]

Another aspect of the present invention relates to a method for imaging pancreatic islets that includes imaging pancreatic islets using the molecular probe for imaging according to the present invention. Still another aspect of the present invention relates to a method for imaging pancreatic islets that includes detecting a signal of the molecular probe for imaging according to the present invention that has been bound to pancreatic islets preliminarily. In the method for imaging, a signal of the molecular probe for imaging according to the present invention that in an enough amount for imaging has been bound to pancreatic islets preliminarily is detected preferably. The imaging of pancreatic islets is as described above. The method for imaging pancreatic islets according to the present invention preferably is a method for imaging pancreatic β-cells from the viewpoint of the application of the same to the examination and diagnosis.

The detection of a signal of the molecular probe for imaging according to the present invention can be performed by, for example, the determination by means of PET and/or the determination by means of SPECT. The determination by means of PET and the determination by means of SPECT include, for example, photographing an image, and determining an amount of pancreatic islets.

The determination by means of SPECT includes, for example, determining, with use of a gamma camera, γ-rays emitted from a subject having pancreatic islets to which the molecular probe for imaging according to the present invention has been bound preliminarily. The determination with use of the gamma camera includes, for example, measuring radiation (γ-rays) emitted from the radioactive nuclides used for labeling the molecular probe for imaging according to the present invention during a certain time unit, and preferably includes determining a direction in which the radiation is emitted and a radiation dose during a certain time unit. The method for imaging according to the present invention further may include presenting the determined distribution of the molecular probe for imaging according to the present invention obtained by the measurement of the radiation as a cross-sectional image, and reconfiguring the obtained cross-sectional image. Examples of the subject include humans and/or mammals other than humans.

The determination by means of PET includes, for example, simultaneously measuring γ-rays generated upon a pair of annihilation between a positron and an electron, with use of a detector for PET, from a subject having pancreatic islets to which the molecular probe for imaging according to the present invention has been bound preliminarily, and further may include figuring a three-dimensional distribution of positions of radioactive nuclides emitting positrons, based on the measurement results.

In the method for imaging according to the present invention, the determination by means of X-ray CT or MRI may be performed, together with the determination by means of SPECT or the determination by means of PET. This makes it possible to obtain, for example, a fusion image obtained by fusion of an image obtained by SPECT or an image obtained by PET (functional image), with an image obtained by CT or an image obtained by MRI (morphological image).

The method for imaging pancreatic islets according to the present invention may include determining a state of pancreatic islets based on the results of the imaging of pancreatic islets with use of the molecular probe for imaging according to the present invention. Determining a state of pancreatic islets based on the results of the imaging of pancreatic islets with use of the molecular probe includes, for example, determining the presence/absence of pancreatic islets by analyzing an image of the imaging of pancreatic islets, and determining an increase/decrease in the amount of pancreatic islets.

The method for imaging pancreatic islets according to the present invention may include administering the molecular probe for imaging according to the present invention to a subject, and it is preferable to administer the molecular probe for imaging according to the present invention in an enough amount for obtaining a desired contrast for imaging. The detection of a signal of the molecular probe for imaging according to the present invention preferably is carried out after a certain lapse of time since the administration of the molecular probe. Examples of the subject include humans and/or mammals other than humans. The administration to a subject may be local administration or systemic administration. A path for administration may be determined appropriately according to a state of a subject and the like, and it may be, for example, intravenous, intraarterial, intradermal, and intraabdominal injection or infusion. The molecular probe for imaging according to the present invention preferably is administered together with a carrier. Examples usable as the carrier include aqueous solvents and non-aqueous solvents. Examples of the aqueous solvent include potassium phosphate buffer solution, physiologic saline, Ringer solution, and distilled water. Examples of the non-aqueous solvent include polyethylene glycol, vegetable fats and oils, ethanol, glycerol, dimethyl sulfoxide, and propylene glycol. The amount of the molecular probe of the present invention for imaging or determining an amount of pancreatic islets may be set to be, for example, not more than 1 µg. The time period from the administration to the determination may be decided appropriately according to, for example, a time that it takes for the molecular probe to bind to pancreatic islets, the type of the molecular probe, the decomposition time of the molecular probe, etc.

[Method for Determining Amount of Pancreatic Islets]

Still another aspect of the present invention relates to a method for determining an amount of pancreatic islets, including detecting a signal of the molecular probe for imaging according to the present invention that has been bound to pancreatic islets preliminarily, and calculating an amount of the pancreatic islets from the detected signal of the molecular probe. The method for determining an amount of pancreatic islets according to the present invention may include imaging of pancreatic islets using the molecular probe for imaging according to the present invention. The imaging of pancreatic islets is as described above. The calculation of an amount of pancreatic islets from results of imaging using the molecular probe may be performed by, for example, analyzing an image obtained by imaging of pancreatic islets. The quantification of a subject of the imaging from results of the imaging can be performed easily by any person skilled in the art, using a calibration curve, an appropriately program, or the like. The method for determining an amount of pancreatic islets according to the present invention preferably is a method for determining an amount of pancreatic β-cells from the viewpoint of the application of the same to the examination and diagnosis.

The method for determining an amount of pancreatic islets according to the present invention further may include presenting the calculated amount of pancreatic islets. Presenting the calculated amount of pancreatic islets includes, for example, storing the calculated amount of pancreatic islets or outputting the same to the outside. Outputting the same to the outside includes, for example, displaying the same on a monitor and printing the same.

[Methods for Prevention, Treatment, and Diagnosis of Diabetes]

Still another aspect of the present invention relates to a method for prevention, treatment, or diagnosis of diabetes. As described above, in the diabetes developing process, the amount of pancreatic islets (particularly, the amount of pancreatic β-cells) decreases prior to the occurrence of glucose tolerance abnormalities, and therefore, when functional abnormalities are detected or there are subjective symptoms, diabetes has already reached the stage where it is too difficult to be treated. With the method for imaging using the molecular probe for imaging according to the present invention and/or the method for determining an amount of the pancreatic islets using the same, however, a decrease in the amount of the pancreatic islets and/or the amount of the pancreatic β-cells can be detected at an early stage, and further, new methods for prevention, treatment, and diagnosis of diabetes can be created. Examples of a subject on which prevention, treatment, and diagnosis of diabetes is carried out include humans and/or mammals other than humans.

A method for diagnosis of diabetes according to the present invention may include imaging of pancreatic islets with use of the molecular probe for imaging according to the present invention; and determining a state of the pancreatic islets based on the obtained image of the pancreatic islets and/or the obtained amount of the pancreatic islets, and performing diagnosis of diabetes based on the determination results. The determination of a state of pancreatic islets includes, for example, determining an increase/decrease, or a change, in the amount of pancreatic islets by comparing the obtained image of pancreatic islets with an image of pancreatic islets as a reference, or comparing the obtained amount of pancreatic islets with an amount of pancreatic islets as a reference. Further, the determination of a state of pancreatic islets may be carried out using an information processing device. When it is determined that the amount of pancreatic islets has decreased, preferably this information is presented, and when it is determined that the amount of pancreatic islets has increased or has been maintained, preferably this information is presented. The diagnosis of diabetes on the basis of the determination results includes, for example, determining a risk of development of diabetes, judging it to be diabetes, and determining a degree of development of diabetes.

A method for treatment of diabetes according to the present invention includes imaging of pancreatic islets with use of the molecular probe for imaging according to the present invention, determining a state of pancreatic islets on the basis of the obtained image of the pancreatic islets and/or the obtained amount of the pancreatic islets so as to perform diagnosis of diabetes, and treating diabetes on the basis of the diagnosis. The determination of a state of pancreatic islets and the diagnosis of diabetes can be performed in the same manner as those in the method for diagnosis of diabetes according to the present invention. The method for treatment of diabetes according to the present invention may include evaluating an effect of treatment such as medication and diet performed on a subject, focusing on a change in an amount of pancreatic islets.

A method for prevention of diabetes according to the present invention includes imaging of pancreatic islets with use of the molecular probe for imaging according to the present invention, and determining a state of pancreatic islets on the basis of the obtained image of the pancreatic islets and/or the obtained amount of the pancreatic islets so as to determine a risk of development of diabetes. The method for prevention of diabetes according to the present invention may include regularly determining an amount of pancreatic islets, and checking presence/absence of a tendency of a decrease in the amount of pancreatic islets.

Still another preferable aspect of the present invention relates to a method for ultra-early diagnosis of diabetes. The method for ultra-early diagnosis of diabetes according to the present invention may include, for example, imaging pancreatic islets and/or determining an amount of pancreatic islets in comprehensive or ordinary medical examination by the method of the present invention, and determining a state of the pancreatic islets on the basis of the obtained image of the pancreatic islets and/or the determined amount of the pancreatic islets. Further, a method for treatment of diabetes according to the present invention may include imaging pancreatic islets and/or determining an amount of pancreatic islets by the method of the present invention, and evaluating functional recovery of the pancreatic islets on the basis of the obtained image of the pancreatic islets and/or the determined amount of the pancreatic islets.

[Kit of the Present Invention]

Still another aspect of the present invention also relates to a kit including the molecular probe for imaging according to the present invention. Examples of embodiments of the kit of this aspect include a kit for performing the method for imaging according to the present invention, a kit for performing the method for determining an amount of pancreatic islets according to the present invention, and a kit for prevention, treatment, or diagnosis of diabetes according to the present invention. Preferably, in each of these embodiments, the kit includes an instruction manual suitable for the embodiment.

In the kit of the present invention, the molecular probe for imaging according to the present invention included therein preferably is in a form of a parenteral solution. Therefore, the kit of the present invention preferably includes a parenteral solution that contains the molecular probe for imaging according to the present invention. The parenteral solution may contain the molecular probe for imaging according to the present invention as an effective ingredient, and further, for example, a medicinal additive such as a carrier. In the present specification, the "medicinal additive" refers to a chemical compound that has obtained authorization as a medicinal additive in the Japanese, U.S. and/or European pharmacopoeias. Examples of the carrier include aqueous solvents and non-aqueous solvents. Examples of the aqueous solvent include potassium phosphate buffer solution, physiologic saline, Ringer solution, and distilled water. Examples of the non-aqueous solvent include polyethylene glycol, vegetable fats and oils, ethanol, glycerol, dimethyl sulfoxide, and propylene glycol. The kit of the present invention further may include a container for containing the molecular probe for imaging according to the present invention, and the container may be filled with the molecular probe for imaging according to the present invention or a parenteral solution that contains the molecular probe for imaging according to the present invention. Examples of the container include a syringe and a vial.

The kit of the present invention may further include, for example, a component used for preparing a molecular probe, such as a buffer or an osmotic regulator, and an instrument used in administration of a molecular probe, such as a syringe.

[Another Aspect of the Kit of the Present Invention]

Still another aspect of the present invention relates to a kit including the aforementioned molecular probe precursor. Examples of embodiments of the kit including the molecular probe precursor of the present invention include a kit for preparing the molecular probe for imaging according to the present invention, a kit for performing the method for imaging according to the present invention, a kit for performing the method for determining an amount of pancreatic islets according to the present invention, and a kit for prevention, treatment, or diagnosis of diabetes according to the present invention. Preferably, in each of these embodiments, the kit including the molecular probe precursor of the present invention includes an instruction manual suitable for each embodiment.

The formulation of the molecular probe precursor of the present invention is not particularly limited, and may be in the form of solution or powder, for example. In terms of ease of handling, the molecular probe precursor is preferably in the form of powder and more preferably in the form of freeze-dried powder (freeze-dried formulation).

The kit including the molecular probe precursor according to the present invention may include, for example, a labeling compound used in the labeling of the precursor of the molecular probe for imaging, the labeling compound having the group represented by the aforementioned chemical formula (I). In the labeling compound having the group represented by the chemical formula (I), the group represented by the chemical formula (I) preferably is a succinimidyl ester compound in which the group represented by the foregoing chemical formula (I) is bonded with succinimide via ester bond, more preferably, a succinimidyl ester compound represented by the aforementioned chemical formula (II), and further more preferably, a succinimidyl ester compound represented by the aforementioned chemical formula (IIa). The kit of the present embodiment more preferably includes, in particular, [$^{18}$F]N-succinimidyl 4-fluorobenzoate, or a starting material for [$^{18}$F] N-succinimidyl 4-fluorobenzoate, as a labeling compound. Examples of the foregoing starting material include ethyl 4-(trimethylammonium triflate)benzoate, ethyl 4-(tosyloxy) benzoate, and ethyl 4-(methylsulfonyloxy)benzoate. The kit of the present embodiment further may include, for example, an instruction manual that describes the method for labeling the precursor of the molecular probe for imaging according to the present invention in which the above-described labeling compound is used.

The kit including the molecular probe precursor according to the present invention preferably includes a labeling compound such as [$^{123}$I]N-succinimidyl 3-iodobenzoate, [$^{124}$I]N-succinimidyl 3-iodobenzoate, [$^{125}$I]N-succinimidyl 3-iodobenzoate, and/or [$^{131}$I]N-succinimidyl 3-iodobenzoate or the starting materials of the labeling compound. Examples of the starting materials include 2,5-dioxopyrrolidin-1-yl 3-(tributylstannyl)benzoate, 2,5-dioxopyrrolidin-1-yl 3-bromobenzoate, 2,5-dioxopyrrolidin-1-yl 3-chlorobenzoate and 2,5-dioxopyrrolidin-1-yl 3-iodobenzoate.

The kit including the molecular probe precursor of the present invention further may include, for example, a reagent to be used for deprotecting the molecular probe for imaging and/or a reagent to be used for the labeling.

The kit including the molecular probe precursor of the present invention further may include, for example, an automatic synthesizing device for synthesizing the labeling compound, and an instruction manual that describes a method for synthesizing the labeling compound having a group represented by the chemical formula (I) using the foregoing automatic synthesizing device for synthesizing the labeling compound. The automatic synthesizing device may be capable of synthesizing the labeling compound, and further, for example, capable of labeling and deprotecting the precursor of the molecular probe for imaging in which the synthesized labeling compound is used. The kit further may include, for example, a reagent containing a radioactive nuclide to be used in synthesizing the labeling compound. Examples of the reagent containing a radioactive nuclide include reagents containing radioactive isotopes such as $^{11}C$, $^{13}N$, $^{15}O$, $^{18}F$, $^{64}Cu$, $^{67}Ga$, $^{68}Ga$, $^{75}Br$, $^{76}Br$, $^{77}Br$, $^{99m}Tc$, $^{111}In$, $^{123}I$, $^{124}I$, $^{125}I$, and $^{131}I$.

Still another aspect of the present invention relates to a kit that includes an automatic peptide synthesizing device for synthesizing the molecular probe precursor of the present invention, and the labeling compound having the group represented by the aforementioned chemical formula (I) and/or an automatic synthesizing device for synthesizing the labeling compound. The automatic synthesizing device may be capable of synthesizing the labeling compound, and further, for example, capable of labeling and deprotecting the precursor of the molecular probe for imaging of pancreatic islets in which the synthesized labeling compound is used. The kit may include an instruction manual that describes a method for synthesizing the molecular probe precursor of the present invention. The instruction manual further may describe, for example, a method for synthesizing the labeling compound having a group represented by the aforementioned chemical formula (I), a labeling method using the same, and a deprotecting method using the same. The kit further may include a reagent containing a radioactive nuclide to be used in synthesis of a labeling compound.

Still another aspect of the present invention relates to a kit that includes the following: an automatic synthesizing device that performs the synthesis of the molecular probe of the present invention, the synthesis of the aforementioned labeling compound, and the labeling and deprotecting of the aforementioned precursor of the molecular probe for imaging in which the aforementioned labeling compound is used; and an instruction manual that describes a method for producing a molecular probe for imaging according to the present invention with use of the foregoing automatic synthesizing device. The instruction manual preferably describes, for example, a method for synthesizing a molecular probe precursor, a method for synthesizing the aforementioned labeling compound, and a method for labeling and deprotecting the molecular probe precursor in which the aforementioned labeling compound is used. The kit further may include a reagent containing a radioactive nuclide to be used in synthesis of the labeling compound.

[Reagent for Imaging of the Present Invention]

Still another aspect of the present invention relates to a reagent for imaging that contains the molecular probe for imaging according to the present invention. The reagent for imaging according to the present invention may contain the molecular probe for imaging according to the present invention as an effective ingredient, and further, a medicinal additive such as a carrier. The carrier is as described above.

Hereinafter, the present invention will be described further by way of Examples and Reference Examples. It should be noted that the present invention is, when interpreted, not limited to the following Examples.

In the description of the present specification, the following abbreviations are used.

OBu: butyl ester group
Boc: butoxycarbonyl group
Trt: trityl group
Pdf: 2,2,4,6,7-pentamethyldihydrobenzofuran-5-sulfonyl group
Mmt: 4-methoxytrityl group
Fmoc: 9-fluorenylmethyloxycarbonyl group

EXAMPLES

Example 1

Using the molecular probe of the formula (3) below (SEQ ID NO. 3), having a configuration in which an amino group of a side chain of a lysine residue at position 40 was labeled with [$^{18}F$]4-fluorobenzoyl (hereinafter referred to also as "[$^{18}F$]FB label") and a carboxyl group at a C-terminus was amidated in the sequence of SEQ NO. 1, biodistribution of the same in a mouse was determined. First, a molecular probe of the formula (3) below was prepared in the following manner.

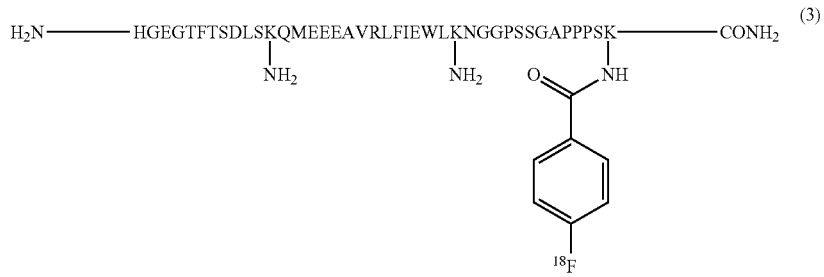

(3)

[Preparation of Molecular Probe]

Polypeptide synthesis was performed by using an automatic peptide synthesizer (Model 433A) manufactured by Applied Biosystems, in accordance with the attached software. For the amino acids having functional groups at the side chains, His(Trt), Asp(OBu), Ser(OBu), Lys(Boc), Gln(Trt), Glu(OBu), Arg(Pbf), Asn(Trt) and Trp(Boc) were used respectively. For the lysines at positions 12 and 27, Lys(Mmt) was used. Rink Amide MBHA (0.125 mmol, 0.34 mmol/g)

was employed as the starting resin, the amino acids were extended serially according to the sequence, whereby the protected peptide resin represented by the following formula (4) was obtained. In the following formula (4), the protecting groups of the side chains other than Lys(Mmt) were not recited.

```
                                              (SEQ ID NO. 4)
Fmoc-HGEGTFTSDLSK(Mmt)QMEEEAVRLFIEWLK(Mmt)

NGGPSSGAPPPSK-resin . . . (4)
```

By a typical process using 1.5% TFA-5% TIS-93.55% $CH_2Cl_2$, the protecting groups (Mmt groups) of the side chains at the lysine residues at positions 12 and 27 were removed from the protected peptide resin of the above formula (4), and the amino groups of the side chains at the free lysine residues at positions 12 and 27 were Fmoc-bonded. Subsequently, removal of all of the protecting groups other than the Fmoc groups of the lysine residues at positions 12 and 27 and the amino group at the N-terminus, and excision of peptide from the resin, were carried out by a typical process using 92.5% TFA-2.5% TIS-2.5% $H_2O$-2.5% ethanediol. After completion of the reaction, the carrier resin was removed by filtration, and dry ether was added thereto for precipitating the crude product, which was then filtered. The thus obtained crude product was purified in a linear gradient system of $CH_3CN$—$H_2O$ containing 0.1% TFA, using a Liquid Chromatograph LC8A manufactured by Shimadzu Corp. (ODS column 3 cm×25 cm). Then, intended fractions were collected by using a fraction collector, and thus the molecular probe precursor of the following formula (5) was obtained as a lyophilized white powder.

```
                                              (SEQ ID NO. 5)
Fmoc-HGEGTFTSDLSK(Fmoc)QMEEEAVRLFIEWLK(Fmoc)

NGGPSSGAPPPSK-NH2 (5)
```

The thus obtained molecular probe precursor (500 μg) of the above-described formula (5) was dissolved in borate buffer (pH 7.8). [$^{18}F$]N-succinimidyl 4-fluorobenzoate ([$^{18}F$] SFB) was added thereto so that pH of the reaction solution was adjusted to 8.5 to 9.0. Thus, the precursor was labeled. Thereafter, DMF and piperidine were added thereto so as to cause a deprotecting reaction, whereby the intended molecular probe of the above-described formula (3) (molecular probe having a configuration in which the lysine residue at position 40 was labeled in the sequence of SEQ ID NO. 1) was obtained. It should be noted that the α-amino group at the N-terminus is not modified in the molecular probe of the foregoing formula (3).

[Biodistribution]

The molecular probe thus prepared (2.9 μCi) of the aforementioned formula (3) was administered to unanesthetized 6-week-old ddY mice (male, weight: 30 g) by intravenous injection (through the tail vein). At points of 5 minutes, 15 minutes, 30 minutes, 60 minutes, and 120 minutes after the administration, organs were dissected out of the mice, respectively (n=5). The weight and the radioactivity of each organ were determined, and an accumulation amount (% dose/g) of the probe was calculated from the radioactivity per unit weight. Exemplary results are shown in Table 1 below and FIG. 1. FIG. 1 is a graph showing how the accumulation of the molecular probe in each organ varied with time.

TABLE 1

| | Time after administration | | | | |
|---|---|---|---|---|---|
| | 5 min. | 15 min. | 30 min. | 60 min. | 120 min. |
| Pancreas | 12.05 | 14.67 | 28.00 | 24.88 | 30.33 |
| | (3.95) | (3.57) | (3.10) | (3.72) | (7.16) |
| Blood | 15.07 | 7.85 | 8.99 | 4.11 | 2.98 |
| | (2.61) | (3.61) | (1.02) | (0.48) | (0.39) |
| Heart | 4.30 | 3.02 | 3.26 | 1.71 | 1.22 |
| | (0.92) | (1.52) | (0.44) | (0.23) | (0.26) |
| Lung | 22.82 | 25.20 | 48.69 | 40.39 | 42.43 |
| | (5.85) | (5.10) | (6.56) | (12.69) | (12.60) |
| Stomach | 1.93 | 1.94 | 5.05 | 9.53 | 8.72 |
| | (1.15) | (0.99) | (1.72) | (2.67) | (4.99) |
| Intestine | 2.68 | 2.10 | 3.60 | 5.21 | 11.30 |
| | (0.86) | (0.71) | (0.82) | (1.28) | (2.72) |
| Liver | 3.69 | 2.25 | 3.13 | 1.37 | 1.24 |
| | (1.05) | (0.82) | (0.53) | (0.08) | (0.11) |
| Spleen | 2.60 | 1.77 | 2.07 | 1.03 | 0.93 |
| | (0.80) | (0.78) | (0.20) | (0.17) | (0.16) |
| Kidney | 28.79 | 35.54 | 43.36 | 20.20 | 19.27 |
| | (6.51) | (17.94) | (5.69) | (2.79) | (1.61) |
| Bone | 3.04 | 1.76 | 2.37 | 1.15 | 0.89 |
| | (0.83) | (0.83) | (0.34) | (0.50) | (0.24) |

Each numerical value indicates an average (SD) of 5 mice.

As shown in Table 1 above and FIG. 1, the accumulation (accumulation amount per unit weight) of the molecular probe of the above-described formula (3) into the pancreas was 12.1% dose/g at a point of 5 minutes after the administration, 14.7% dose/g at a point of 15 minutes after the administration, and 28.0% dose/g at a point of 30 minutes after the administration. During a time period from the point of 15 minutes to the point of 120 minutes after the administration, the molecular probe of the foregoing formula (3) accumulated most in the pancreas among the organs other than the lungs and the kidneys. During a time period from the point of 60 minutes to the point of 120 minutes after the administration, the molecular probe of the foregoing formula (3) accumulated most in the pancreas among the organs other than the lungs. During a time period from the point of 15 minutes to the point of 120 minutes after the administration, the accumulation of the probe in the pancreas was maintained at a level exceeding 25% dose/g. Further, the molecular probe of the foregoing formula (3) exhibited a high ratio of the accumulation of the same in the pancreas to the accumulation of the same in blood (accumulation of the probe in the pancreas/ accumulation of the probe in blood); the ratio exceeded three at the point of 60 minutes after the administration and later on, and particularly, it exceeded 5 during a time period from the point of 60 minutes to the point of 120 minutes after the administration. This suggests that the molecular probe of the foregoing formula (3) allowed, for example, a desired contrast for imaging by PET to be obtained. Besides, as shown in Table 1 above and FIG. 1, it was suggested that the molecular probe of the foregoing formula (3) exhibited low radioactivity accumulation in bones, and was not subjected to defluorination metabolism in vivo. Therefore, the molecular probe of Example 1 represented by the aforementioned formula (3) is considered suitable for the imaging of pancreatic β-cells.

Reference Example 1

For Reference Example 1, a molecular probe was prepared from a molecular probe precursor of the following formula (6) of SEQ NO. 6, in which protecting groups (Fmoc) were bonded to an α-amino group at an N-terminus and to a lysine residue at position 19 and a carboxyl group at a C-terminus was amidated, and the molecular probe was used for determining biodistribution thereof in a mouse. In other words, using the molecular probe represented by the following formula (7) (SEQ ID NO. 7), having a configuration in which [$^{18}$F] FB was bonded to an amino group of a side chain of a lysine at position 4 and a carboxyl group at a C-terminus was amidated in the amino acid sequence of SEQ ID NO. 6, the biodistribution of this molecular probe in a mouse was determined. Preparation of the molecular probe precursor and the molecular probe, and also determination of the biodistribution were carried out in the same manner as Example 1. Exemplary results are shown in Table 2 below and FIG. 2.

(SEQ ID NO. 6)
Fmoc-DLSKQMEEEAVRLFIEWLK(Fmoc)NGGPSSGAPPPS-NH$_2$ (6)

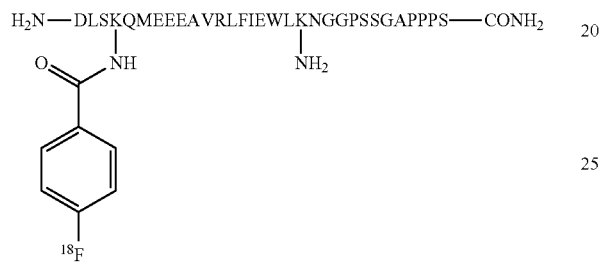

(7)

was bonded to an amino group of a side chain of a lysine at position 19 and a carboxyl group at a C-terminus was amidated in the amino acid sequence of SEQ ID NO. 8, biodistribution of this molecular probe in a mouse was determined. Preparation of the molecular probe precursor and the molecular probe and also determination of the biodistribution were carried out in the same manner as Example 1. Exemplary results are shown in Table 3 below and FIG. 3.

(SEQ ID NO. 8)
Fmoc-DLSK(Fmoc)QMEEEAVRLFIEWLKNGGPSSGAPPPS-NH$_2$ (8)

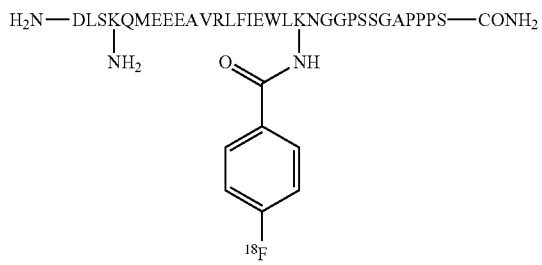

(9)

TABLE 2

| | Time after administration | | | | |
|---|---|---|---|---|---|
| | 5 min. | 15 min. | 30 min. | 60 min. | 120 min. |
| Pancreas | 3.98 | 4.92 | 4.65 | 2.42 | 1.35 |
| | (0.27) | (0.48) | (1.83) | (0.57) | (0.37) |
| Blood | 9.95 | 5.52 | 4.08 | 1.64 | 0.57 |
| | (0.75) | (0.26) | (0.93) | (0.14) | (0.16) |
| Heart | 4.05 | 2.43 | 1.85 | 0.79 | 0.30 |
| | (0.34) | (0.22) | (0.67) | (0.06) | (0.08) |
| Lung | 8.33 | 5.87 | 4.49 | 2.44 | 1.24 |
| | (0.77) | (0.47) | (0.57) | (0.49) | (0.20) |
| Stomach | 2.18 | 2.11 | 1.09 | 3.27 | 9.08 |
| | (1.28) | (1.08) | (0.43) | (4.79) | (9.78) |
| Intestine | 1.99 | 1.51 | 1.58 | 1.92 | 4.73 |
| | (0.16) | (0.10) | (0.50) | (1.19) | (1.17) |
| Liver | 8.57 | 5.82 | 4.15 | 1.96 | 0.59 |
| | (0.80) | (0.46) | (0.62) | (0.32) | (0.22) |
| Spleen | 3.52 | 2.48 | 1.87 | 0.86 | 0.33 |
| | (0.36) | (0.31) | (0.47) | (0.25) | (0.08) |
| Kidney | 43.16 | 37.86 | 24.10 | 11.25 | 5.27 |
| | (5.40) | (6.69) | (3.82) | (2.52) | (1.88) |
| Bone | 2.41 | 2.01 | 1.36 | 1.07 | 0.32 |
| | (0.17) | (0.18) | (0.33) | (0.73) | (0.18) |

Each numerical value indicates an average (SD) of 5 mice.

Reference Example 2

For Reference Example 2, a molecular probe was prepared from a molecular probe precursor of the following formula (8), having a configuration in which protecting groups (Fmoc) were bonded to an α-amino group at an N-terminus and a lysine residue at position 4 and a carboxyl group at a C-terminus was amidated in the amino acid sequence of SEQ ID NO. 8, and the molecular probe was used for determining biodistribution thereof in a mouse. In other words, using the molecular probe represented by the following formula (9) (SEQ ID NO. 9), having a configuration in which [$^{18}$F] FB

TABLE 3

| | Time after administration | | | | |
|---|---|---|---|---|---|
| | 5 min. | 15 min. | 30 min. | 60 min. | 120 min. |
| Pancreas | 3.97 | 4.13 | 3.92 | 3.32 | 1.64 |
| | (0.89) | (0.56) | (0.51) | (1.16) | (0.15) |
| Blood | 8.84 | 6.34 | 4.40 | 2.66 | 1.42 |
| | (0.49) | (1.41) | (0.54) | (0.74) | (0.13) |
| Heart | 3.56 | 2.92 | 1.82 | 1.09 | 0.63 |
| | (0.38) | (0.61) | (0.21) | (0.28) | (0.08) |
| Lung | 7.56 | 6.60 | 5.62 | 3.46 | 2.33 |
| | (1.14) | (0.47) | (0.31) | (0.56) | (0.28) |
| Stomach | 0.87 | 1.09 | 1.04 | 1.16 | 1.00 |
| | (0.12) | (0.20) | (0.21) | (0.54) | (0.66) |
| Intestine | 1.29 | 1.25 | 1.04 | 1.47 | 2.09 |
| | (0.19) | (0.36) | (0.19) | (0.25) | (0.54) |
| Liver | 25.23 | 16.81 | 11.71 | 7.56 | 3.72 |
| | (3.40) | (1.90) | (2.74) | (1.63) | (0.58) |
| Spleen | 3.06 | 2.42 | 1.81 | 1.22 | 0.75 |
| | (0.79) | (0.23) | (0.34) | (0.28) | (0.23) |
| Kidney | 30.30 | 38.04 | 29.70 | 17.14 | 11.35 |
| | (3.53) | (7.06) | (5.57) | (4.74) | (4.10) |
| Bone | 1.87 | 1.65 | 1.23 | 0.89 | 0.56 |
| | (0.12) | (0.21) | (0.23) | (0.16) | (0.15) |

Each numerical value indicates an average (SD) of 5 mice.

Figure 2:
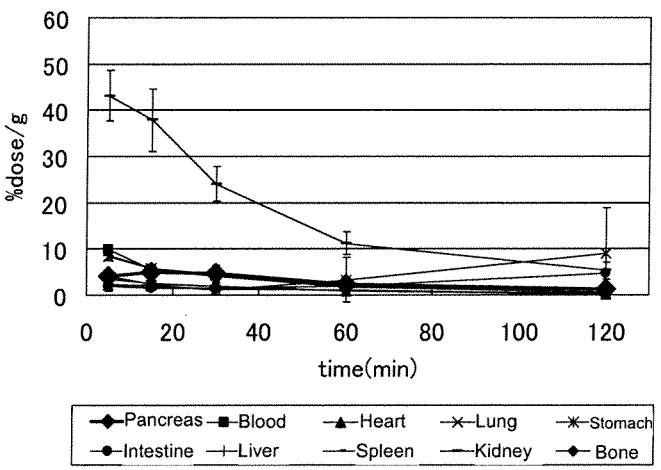
FIG. 2 is a graph showing exemplary resultant variations with time of biodistribution of a molecular probe of Reference Example 1.
Figure 3:
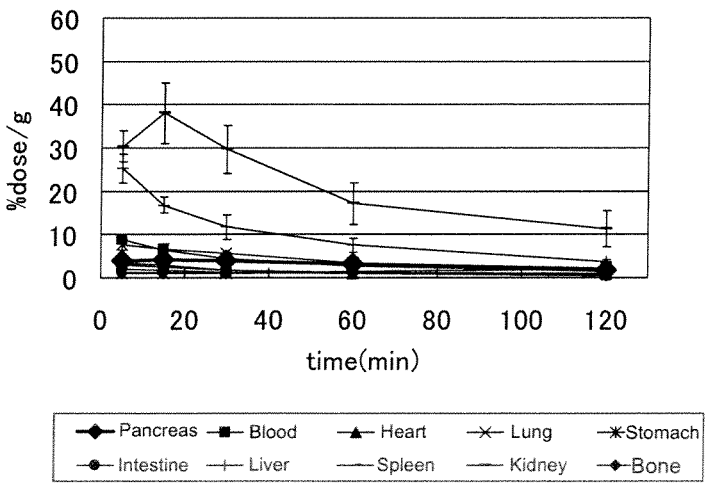
FIG. 3 is a graph showing exemplary resultant variations with time of biodistribution of a molecular probe of Reference Example 2.

As shown in Tables 1 to 3 above and FIGS. 1 to 3, the molecular probe prepared in Example 1, which is represented by the aforementioned formula (3), accumulated more in amount in the pancreas, and less in the liver as an organ adjacent to the pancreas, as compared with the molecular probe of Reference Example 1 represented by the aforementioned formula (7) and the molecular probe of Reference Example 2 represented by the aforementioned formula (9). Particularly, at the point of 30 minutes after the administration and later on, the accumulation amount in the pancreas of the molecular probe of Example 1 represented by the aforementioned formula (3) was 5 times or more the accumulation amount of the molecular probe of Reference Example 1 or 2. This indicates that the molecular probe prepared in Example 1 accumulated specifically in the pancreas.

By administering the molecular probe represented by the aforementioned formula (7) to a mouse, a three-dimensional image of the pancreas of the mouse was obtained. Further, by administering the molecular probe represented by the aforementioned formula (9) to a mouse, a noninvasive three-dimensional image of the pancreas of the mouse was obtained. As mentioned above, the molecular probe prepared in Example 1 represented by the aforementioned formula (3), in which a side chain of a lysine at a C-terminus was labeled, accumulated extremely much in the pancreas and accumulated less in the lever as the organ adjacent to the pancreas, in comparison with the molecular probes of Reference Examples 1 and 2 represented by the formulae (7) and (9), respectively. This suggests that the molecular probe of Example 1 enabled noninvasive three-dimensional imaging of pancreatic islets.

These results suggest that a molecular probe of the present invention enables noninvasive three-dimensional imaging of the pancreas, particularly noninvasive three-dimensional imaging of pancreatic β-cells, in a human.

Reference Example 3

Figure 4:
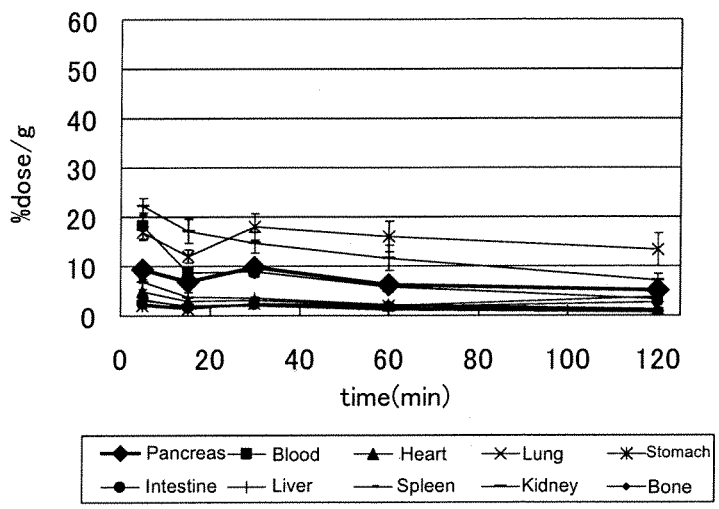
FIG. 4 is a graph showing exemplary resultant variations with time of biodistribution of a molecular probe of Reference Example 3.

For Reference Example 3, using a molecular probe represented by the following formula (10) (SEQ ID NO. 10), biodistribution of this molecular probe in mice was measured in the same manner as Example 1. Exemplary results are shown in Table 4 below and FIG. 4.

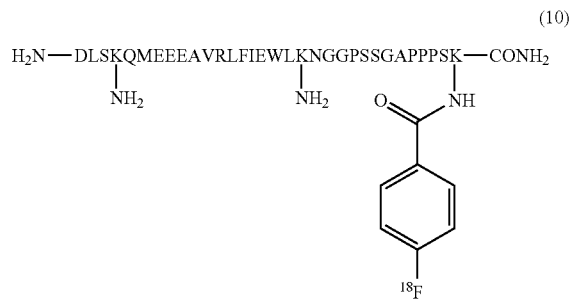

(10)

TABLE 4

| | Time after administration | | | | |
|---|---|---|---|---|---|
| | 5 min. | 15 min. | 30 min. | 60 min. | 120 min. |
| Pancreas | 9.31 | 6.93 | 9.68 | 6.33 | 5.08 |
| | (0.57) | (1.15) | (0.92) | (0.65) | (1.23) |
| Blood | 18.12 | 8.70 | 8.87 | 5.79 | 3.23 |
| | (2.72) | (1.18) | (0.99) | (1.15) | (0.25) |
| Heart | 4.92 | 2.86 | 3.04 | 1.94 | 1.14 |
| | (0.49) | (0.59) | (0.35) | (0.47) | (0.10) |
| Lung | 16.79 | 11.99 | 17.96 | 16.03 | 13.32 |
| | (1.19) | (1.39) | (2.69) | (3.16) | (3.29) |
| Stomach | 2.00 | 1.44 | 2.46 | 2.02 | 3.88 |
| | (0.45) | (0.30) | (0.33) | (0.33) | (0.47) |
| Intestine | 2.52 | 1.57 | 2.13 | 1.78 | 2.69 |
| | (0.53) | (0.27) | (0.23) | (0.15) | (0.53) |
| Liver | 6.95 | 3.72 | 3.62 | 2.17 | 1.40 |
| | (0.39) | (0.88) | (0.25) | (0.42) | (0.23) |
| Spleen | 3.24 | 1.79 | 1.97 | 1.09 | 0.70 |
| | (0.45) | (0.42) | (0.32) | (0.16) | (0.09) |
| Kidney | 22.14 | 17.11 | 14.77 | 11.64 | 7.08 |
| | (1.75) | (2.44) | (2.12) | (2.61) | (1.47) |

TABLE 4-continued

| | Time after administration | | | | |
|---|---|---|---|---|---|
| | 5 min. | 15 min. | 30 min. | 60 min. | 120 min. |
| Bone | 3.18 | 2.00 | 2.20 | 1.49 | 0.93 |
| | (0.42) | (0.35) | (0.20) | (0.27) | (0.13) |

Each numerical value indicates an average (SD) of 5 mice.

As shown in Tables 1 and 4 above, the molecular probe of Example 1, which is represented by the aforementioned formula (3), accumulated more in amount in the pancreas, and less in the liver as an organ adjacent to the pancreas, as compared with the molecular probe of Reference Example 3 represented by the aforementioned formula (10). Particularly, at the point of 30 minutes after the administration and later on, the accumulation amount in the pancreas of the molecular probe of Example 1 represented by the aforementioned formula (3) was about 2.5 times or more the accumulation amount of the molecular probe of Reference Example 3. This indicates that the molecular probe prepared in Example 1 accumulated specifically in the pancreas.

Based on the accumulation amount obtained by the biodistribution experiments on the molecular probe of Example 1 and the molecular probes of Reference Examples 1 to 3, the ratio of pancreas/liver (accumulation amount in pancreas/accumulation amount in liver) for each probe is shown in Table 5 below, the ratio of pancreas/kidney (accumulation amount in pancreas/accumulation amount in kidney) for each probe is shown in Table 6 below, and the ratio of pancreas/blood (accumulation amount in pancreas/accumulation amount in blood) for each probe is shown in Table 7 below.

TABLE 5

| | Pancreas/Liver Ratio | | | | |
|---|---|---|---|---|---|
| | Time after administration | | | | |
| | 5 min. | 15 min. | 30 min. | 60 min. | 120 min. |
| Ex. 1 | 3.31 | 6.83 | 9.11 | 18.27 | 24.71 |
| | (1.02) | (1.61) | (1.58) | (3.57) | (6.50) |
| Ref. Ex. 1 | 0.46 | 0.85 | 1.12 | 1.24 | 2.28 |
| Ref. Ex. 2 | 0.16 | 0.25 | 0.34 | 0.44 | 0.44 |
| Ref. Ex. 3 | 1.34 | 1.90 | 2.67 | 2.97 | 3.61 |

TABLE 6

| | Pancreas/Kidney Ratio | | | | |
|---|---|---|---|---|---|
| | Time after administration | | | | |
| | 5 min. | 15 min. | 30 min. | 60 min. | 120 min. |
| Ex. 1 | 0.41 | 0.45 | 0.66 | 1.24 | 1.58 |
| | (0.07) | (0.13) | (0.14) | (0.14) | (0.40) |

TABLE 6-continued

Pancreas/Kidney Ratio

| | Time after administration | | | | |
|---|---|---|---|---|---|
| | 5 min. | 15 min. | 30 min. | 60 min. | 120 min. |
| Ref. Ex. 1 | 0.09 | 0.13 | 0.19 | 0.22 | 0.26 |
| Ref. Ex. 2 | 0.13 | 0.11 | 0.13 | 0.19 | 0.14 |
| Ref. Ex. 3 | 0.42 | 0.40 | 0.66 | 0.54 | 0.72 |

TABLE 7

Pancreas/Blood Ratio

| | Time after administration | | | | |
|---|---|---|---|---|---|
| | 5 min. | 15 min. | 30 min. | 60 min. | 120 min. |
| Ex. 1 | 0.79 | 2.03 | 3.15 | 6.09 | 10.44 |
| | (0.20) | (0.58) | (0.53) | (0.94) | (3.05) |
| Ref. Ex. 1 | 0.40 | 0.89 | 1.14 | 1.47 | 2.36 |
| Ref. Ex. 2 | 0.45 | 0.65 | 0.89 | 1.25 | 1.16 |
| Ref. Ex. 3 | 0.52 | 0.79 | 1.11 | 1.12 | 1.56 |

As shown in Table 5 above, the ratio of pancreas/liver for the molecular probe of Example 1 (the molecular probe of the above formula (3)) increased remarkably with time in comparison with the molecular probes of Reference Examples 1 to 3. Particularly, the ratio of pancreas/liver of the molecular probe of Example 1 exceeded 3.4 times at the point of 30 minutes after the administration and later on and 6 times at the point of 60 minutes after the administration and later on as much as those of the molecular probes of Reference Examples 1 to 3. As shown in Table 6 above, the ratio of pancreas/kidney for the molecular probe of Example 1 increased with time in comparison with the molecular probes of Reference Examples 1 to 3 and the ratio of pancreas/kidney for the molecular probe of Example 1 became more than 1 at the point of 60 minutes after the administration and later on. As shown in Table 7 above, the ratio of pancreas/blood for the molecular probe of Example 1 increased remarkably with time in comparison with the molecular probes of Reference Examples 1 to 3. The ratio of pancreas/blood for the molecular probe of Example 1 became more than 1 at an early stage after the administration and indicated a satisfactory blood clearance. Thus, it was suggested that clear images of pancreas can be obtained at the time of imaging with the molecular probe of Example 1 with an excellent blood clearance, which accumulates in the pancreas in a large amount while accumulates less in the surrounding organs of the pancreas.

These results suggest that the molecular probe for imaging according to the present invention enables noninvasive three-dimensional imaging of the pancreas, particularly noninvasive three-dimensional imaging of pancreatic β-cells, in a human.

Example 2

[Preparation of Molecular Probe]

Except using [$^{125}$I]N-succinimidyl 3-iodobenzoate ([$^{125}$I]SIB) in place of [$^{18}$F]SFB, a molecular probe of the following formula (11) (SEQ ID NO. 11) was prepared in the same manner as Example 1. The molecular probe of the following formula (11) had a configuration in which an amino group of a side chain of a lysine residue at position 40 was labeled with [$^{125}$I]3-iodobenzoyl group (hereinafter also referred to as [$^{125}$I]IB labeling), a carboxyl group at a C-terminus is amidated and an α-amino group at a N-terminus was not modified in an amino acid sequence represented by SEQ ID NO. 1.

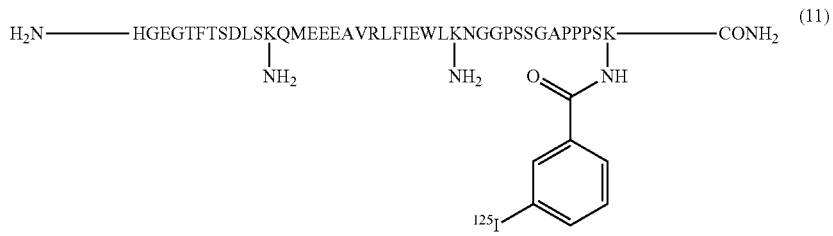

(11)

[Biodistribution]

Figure 5:
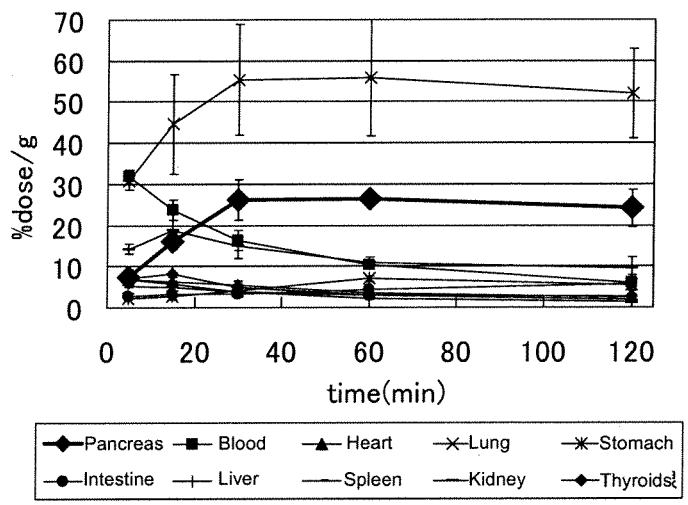
FIG. 5 is a graph showing exemplary resultant variations with time of biodistribution of a molecular probe for imaging of Example 2.

The molecular probe thus prepared (0.48 µCi) of the aforementioned formula (11) was administered to unanesthetized 6-week-old ddY mice (male, weight: 30 g) by intravenous injection (through the tail vein). At points of 5 minutes, 15 minutes, 30 minutes, 60 minutes, and 120 minutes after the administration, each organ was dissected out of the mice, respectively (n=5). The weight and the radioactivity of each organ were determined, and an accumulation amount (% dose/g) of the molecular probe was calculated from the radioactivity per unit weight. Exemplary results are shown in Table 8 below and FIG. 5. FIG. 5 is a graph showing how the accumulation of the molecular probe in each organ varied with time.

TABLE 8

| | Time after administration | | | | |
|---|---|---|---|---|---|
| | 5 min. | 15 min. | 30 min. | 60 min. | 120 min. |
| Pancreas | 7.40 | 16.20 | 26.13 | 26.50 | 24.15 |
| | (1.86) | (2.16) | (4.95) | (1.58) | (4.53) |
| Blood | 31.73 | 23.63 | 16.26 | 10.46 | 6.08 |
| | (1.85) | (2.45) | (2.40) | (0.84) | (1.19) |
| Heart | 6.72 | 6.24 | 5.42 | 3.47 | 2.34 |
| | (0.64) | (1.02) | (1.13) | (0.22) | (0.42) |
| Lung | 30.76 | 44.55 | 55.33 | 55.93 | 52.08 |
| | (2.05) | (12.17) | (13.48) | (14.15) | (10.84) |
| Stomach | 2.15 | 2.67 | 4.12 | 6.97 | 5.35 |
| | (0.28) | (0.74) | (1.64) | (0.62) | (0.71) |

TABLE 8-continued

|  | Time after administration | | | | |
|---|---|---|---|---|---|
|  | 5 min. | 15 min. | 30 min. | 60 min. | 120 min. |
| Intestine | 2.64 | 3.19 | 3.33 | 4.26 | 5.64 |
|  | (0.45) | (0.67) | (0.52) | (0.47) | (2.24) |
| Liver | 6.79 | 5.78 | 3.93 | 3.09 | 2.04 |
|  | (1.12) | (0.63) | (0.53) | (0.44) | (0.46) |
| Spleen | 5.26 | 4.80 | 3.70 | 2.20 | 1.40 |
|  | (0.27) | (0.79) | (0.71) | (0.22) | (0.32) |
| Kidney | 14.27 | 18.90 | 14.94 | 11.02 | 9.65 |
|  | (1.33) | (2.28) | (2.82) | (1.19) | (2.59) |
| Thyroid gland | 7.06 | 8.07 | 4.96 | 2.88 | 2.71 |
|  | (1.33) | (2.08) | (1.26) | (0.54) | (1.33) |

Each numerical value indicates an average (SD) of 5 mice.

As shown in Table 8 above and FIG. 5, during a time period from the point of 30 minutes to the point of 120 minutes after the administration, the accumulation of the molecular probe of Example 2 represented by the foregoing formula (11) accumulated most in the pancreas among the organs other than the lungs, and the accumulation of the molecular probe in the pancreas was maintained at a level exceeding 24% dose/g. Further, as shown in Table 8 above and FIG. 5, no great change was seen in the accumulation of the molecular probe of the foregoing formula (11) in the thyroid gland, and this suggests that the molecular probe of the foregoing formula (11) was not subjected to deiodization metabolism in vivo. Therefore, the molecular probe prepared in Example 2 represented by the foregoing formula (11) is considered suitable for imaging of the pancreatic β-cells, preferably imaging of GLP-1R of the pancreatic β-cells.

Reference Example 4

Figure 6:
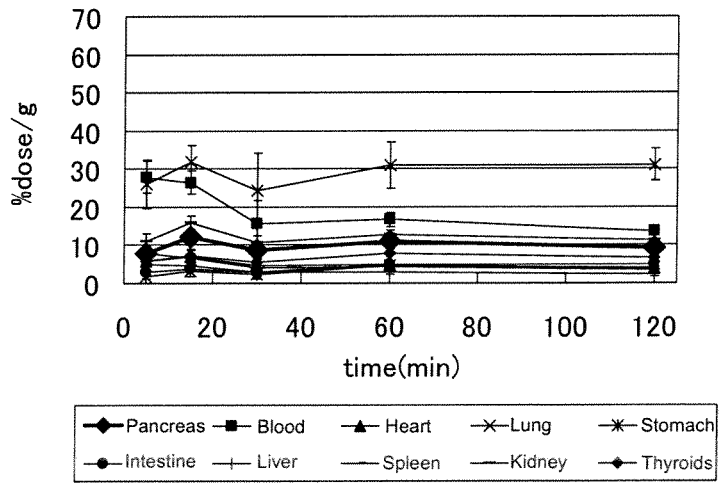
FIG. 6 is a graph showing exemplary resultant variations with time of biodistribution of a molecular probe of Reference Example 4.

For Reference Example 4, using a molecular probe represented by the following formula (12) (SEQ ID NO. 12), biodistribution of this molecular probe in mice was measured in the same manner as Example 1. Exemplary results are shown in Table 9 below and FIG. 6.

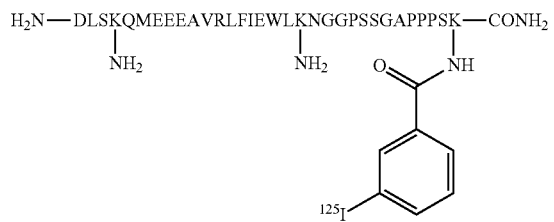

(12)

TABLE 9

|  | Time after administration | | | | |
|---|---|---|---|---|---|
|  | 5 min. | 15 min. | 30 min. | 60 min. | 120 min. |
| Pancreas | 7.73 | 12.28 | 8.73 | 10.90 | 9.23 |
|  | (2.18) | (3.74) | (3.65) | (1.96) | (1.19) |
| Blood | 27.91 | 26.44 | 15.53 | 16.65 | 13.67 |
|  | (4.16) | (3.06) | (6.05) | (1.77) | (0.99) |
| Heart | 5.74 | 6.92 | 4.56 | 4.80 | 3.66 |
|  | (1.38) | (0.79) | (2.00) | (0.17) | (0.49) |
| Lung | 25.98 | 31.88 | 24.29 | 30.69 | 31.02 |
|  | (6.37) | (4.17) | (9.94) | (6.20) | (4.18) |

TABLE 9-continued

|  | Time after administration | | | | |
|---|---|---|---|---|---|
|  | 5 min. | 15 min. | 30 min. | 60 min. | 120 min. |
| Stomach | 1.72 | 3.26 | 2.30 | 4.58 | 4.15 |
|  | (0.52) | (1.65) | (1.04) | (0.96) | (1.70) |
| Intestine | 2.76 | 3.74 | 2.85 | 4.94 | 5.00 |
|  | (0.56) | (0.41) | (1.18) | (0.84) | (1.23) |
| Liver | 7.71 | 6.54 | 4.18 | 4.32 | 3.42 |
|  | (1.23) | (0.66) | (1.72) | (0.41) | (0.27) |
| Spleen | 4.86 | 4.61 | 3.03 | 2.80 | 2.20 |
|  | (0.50) | (0.70) | (1.05) | (0.39) | (0.36) |
| Kidney | 11.09 | 15.83 | 10.80 | 12.86 | 11.14 |
|  | (1.94) | (1.69) | (4.50) | (1.13) | (1.40) |
| Thyroid gland | 5.81 | 7.26 | 5.41 | 7.80 | 6.58 |
|  | (1.93) | (1.83) | (1.67) | (2.12) | (2.35) |

Each numerical value indicates an average (SD) of 5 mice.

As shown in Tables 8 and 9 above, the molecular probe of Example 2, which is represented by the foregoing formula (11), accumulated more in amount in the pancreas as compared with the molecular probe of Reference Example 4 represented by the foregoing formula (12). Particularly, at the point of 30 minutes after the administration and later on, the accumulation amount in the pancreas of the molecular probe of the aforementioned formula (11) exceeded about 2.5 times as much as the accumulation amount of the molecular probe of Reference Example 4. Further, the molecular probe of the foregoing formula (11) accumulated less in the liver as an organ adjacent to the pancreas, as compared with the molecular probe of Reference Example 4. This indicates that the molecular probe prepared in Example 2, which is represented by the foregoing formula (11), accumulated specifically in the pancreas.

Based on the accumulation amount obtained by the biodistribution experiments on the molecular probe of Example 2 and the molecular probe of Reference Examples 4, the ratio of pancreas/liver for each probe is shown in Table 10 below, the ratio of pancreas/kidney for each probe is shown in Table 11 below, and the ratio of pancreas/blood for each probe is shown in Table 12 below.

TABLE 10

| Pancreas/Liver Ratio | | | | | |
|---|---|---|---|---|---|
|  | Time after administration | | | | |
|  | 5 min. | 15 min. | 30 min. | 60 min. | 120 min. |
| Ex. 2 | 1.09 | 2.80 | 6.65 | 8.58 | 11.83 |
|  | (1.02) | (1.61) | (1.58) | (3.57) | (6.50) |
| Ref. Ex. 4 | 1.00 | 1.88 | 2.09 | 2.52 | 2.69 |

TABLE 11

| Pancreas/Kidney Ratio | | | | | |
|---|---|---|---|---|---|
|  | Time after administration | | | | |
|  | 5 min. | 15 min. | 30 min. | 60 min. | 120 min. |
| Ex. 2 | 0.52 | 0.86 | 1.75 | 2.40 | 2.50 |
|  | (0.07) | (0.13) | (0.14) | (0.14) | (0.40) |
| Ref. Ex. 4 | 0.70 | 0.78 | 0.81 | 0.85 | 0.83 |

TABLE 12

| | Pancreas/Blood Ratio | | | | |
|---|---|---|---|---|---|
| | Time after administration | | | | |
| | 5 min. | 15 min. | 30 min. | 60 min. | 120 min. |
| Ex. 2 | 0.23 (0.20) | 0.69 (0.58) | 1.61 (0.53) | 2.53 (0.94) | 3.97 (3.05) |
| Ref. Ex. 4 | 0.28 | 0.46 | 0.56 | 0.65 | 0.68 |

As shown in Table 10 above, the ratio of pancreas/liver for the molecular probe of Example 2 (the molecular probe of the formula (11)) increased remarkably with time in comparison with the molecular probe of Reference Example 4. Particularly, at the point of 30 minutes after the administration and later on, the ratio of pancreas/liver of the molecular probe of Example 2 exceeded 2.5 times as much as that of the molecular probe of Reference Example 4. As shown in Table 11 above, the ratio of pancreas/kidney for the molecular probe of Example 2 increased with time in comparison with the molecular probe of Reference Example 4 and the ratio of pancreas/kidney for the molecular probe of Example 2 became more than 1 at the point of 30 minutes after the administration and later on. As shown in Table 12 above, the ratio of pancreas/blood for the molecular probe of Example 2 increased remarkably with time in comparison with the molecular probes of Reference Example 4. The ratio of pancreas/blood for the molecular probe of Example 2 became more than 1 at the point of 30 minutes after the administration and later on and indicated a satisfactory blood clearance. Thus, it was suggested that clear images of pancreas can be obtained at the time of imaging with the molecular probe of Example 2 with an excellent blood clearance, which accumulates in the pancreas in a large amount while accumulates less in the surrounding organs of the pancreas.

[Two-Dimensional Imaging Analysis]

The molecular probe thus prepared (4 µCi/150 µL) of the foregoing formula (11) was administered to unanesthetized MIP-GFP mice (male, weight: 20 g) by intravenous injection. At points of 30 minutes and 60 minutes after the administration, the pancreas were dissected out of the mice, respectively (n=2). Sections were cut out of the dissected pancreases, and each section was placed on a slide glass, covered with a cover glass. Fluorescence and radioactivity (autoradiography) of each section were determined using an image analyzer (trade name: Typhoon 9410, produced by GE Health Care Inc.) (exposure time: 18 hours). Exemplary results are shown in FIG. 7.

Non-labeled exendin(9-39) (cold probe, SEQ ID NO. 15) was administered (0.1 mL of 0.5 mg/mL) preliminarily by intravenous injection to unanesthetized MIP-GFP mice (male, weight: 20 g), and these mice were used as controls. At a point of 30 minutes after the preliminary administration, the molecular probe of the foregoing formula (11) (4 µCi/150 µL) was administered to the mice by intravenous injection. Then, at points of 30 minutes and 60 minutes after the administration of the molecular probe of the foregoing formula (11), the pancreases were dissected out of the mice, respectively (n=2). Sections were cut out of the dissected pancreases, and fluorescence and radioactivity of each section were determined in the same manner as described above. Exemplary results are shown in FIG. 7 together with the results on administering only the molecular probe of the formula (11).

Figure 7:
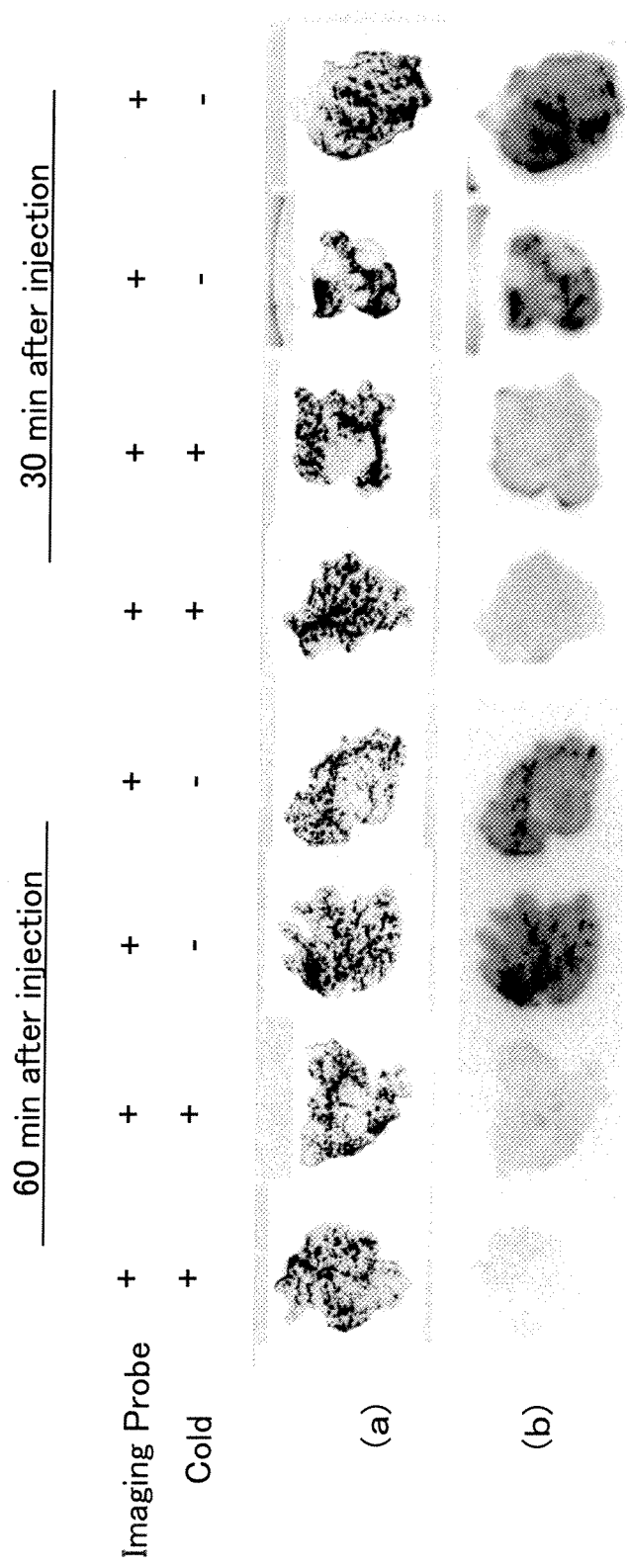
FIG. 7 is an image showing exemplary results on imaging of pancreatic sections using the molecular probe for imaging of Example 2.

FIG. 7 is images showing exemplary results on image analysis of the pancreas sections of the MIP-GFP mice to which the molecular probe of the foregoing formula (11) was administered and those of the MIP-GFP mice (controls) to which the cold probe was preliminary administered. In FIG. 7, the images on the left side show a fluorescent signal (a) and a radioactivity signal (b) of each of the sections cut out of the pancreas at a point of 60 minutes after the administration and the images on the right side show a fluorescent signal (a) and a radioactivity signal (b) of each of the sections cut out of the pancreas at a point of 30 minutes after the administration. In each side, the left images are of the pancreas sections of the mice to which the cold probe was preliminary administered (controls) and the right images are of the pancreas sections of the mice to which only the molecular probe of the formula (11) was administered.

As shown in (a) of FIG. 7, a fluorescence GFP signal was observed by an image analyzer in each of the pancreas sections of the MIP-GFP mice. As shown in (b) of FIG. 7, substantially no radioactivity signal was detected from the sections of the controls to which the cold probe was preliminary administered. From this observation, it was found that the binding with GLP-1 receptors was inhibited by the preliminary administration of the cold probe, whereby the uptake of the molecular probe of the formula (11) was inhibited. Further, as shown in (a) and (b) of FIG. 7, the localization of the radioactivity signal detected from the labeled molecular probe of the formula (11) was consistent with that of the GFP signal. From this, it was confirmed that the molecular probe of the formula (11) accumulated specifically in the GLP-1 receptors of the pancreatic β-cells.

Here, all of $^{125}$I, $^{123}$I, and $^{131}$I were γ-ray emitting nuclides. Still further, $^{125}$I and $^{123}$I have the same numbers of nuclear spins. In view of these, it can be presumed that even a molecular probe obtained by replacing the radioactive iodine atom ($^{125}$I) used in the labeling of the molecular probe of the formula (11) with $^{123}$I or $^{131}$I will exhibit behaviors substantially identical to those of the molecular probe of the formula (13). Further, it also can be presumed that even a molecular probe obtained by replacing the radioactive iodine atom ($^{125}$I) with $^{124}$I will exhibit behaviors substantially identical to those of the molecular probe of the formula (11). Thus, it was suggested that using the molecular probe obtained by replacing $^{125}$I of the molecular probe of the formula (11) with $^{123}$I, $^{124}$I, or $^{131}$I, the noninvasive three-dimensional imaging of pancreatic β-cells by SPECT, PET, or the like is enabled, and preferably, the quantification of pancreatic β-cells is enabled.

Example 3

[Preparation of Molecular Probe]

Except using [$^{123}$I]N-succinimidyl 3-iodobenzoate ([$^{123}$I]SIB) in place of [$^{18}$F]SFB, a molecular probe of the following formula (13) (SEQ ID NO. 13) was prepared in the same manner as Example 1. The molecular probe of the following formula (13) had a configuration in which an amino group of a side chain of a lysine residue at position 40 was labeled with [$^{123}$I]3-iodobenzoyl group (hereinafter also referred to as [$^{123}$I]IB labeling), a carboxyl group at a C-terminus is amidated and an α-amino group at a N-terminus is not modified in an amino acid sequence represented by SEQ ID NO. 1.

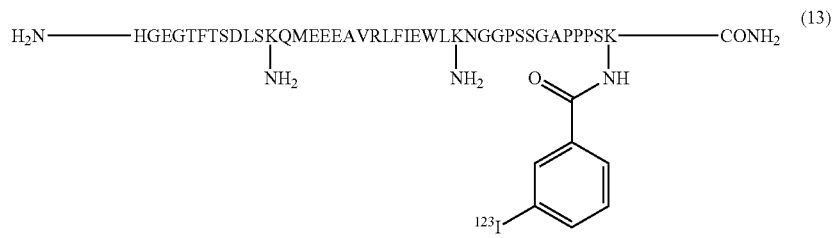

[Three-Dimensional Imaging]

Using the molecular probe of the formula (13), SPECT imaging of mice was carried out. The molecular probe of the formula (13) (276 µCi/310 µL) was administered to anesthetized 6-week-old ddY mice (male, weight: about 30 g) by intravenous injection, and the SPECT imaging was carried out. The SPECT imaging was carried out under the following imaging conditions for 32 minutes starting at the point of 30 minutes after the administration, with use of a gamma camera (product name: SPECT 2000H-40, manufactured by Hitachi Medical Corporation). Images obtained were reconfigured under the following reconfiguration conditions.

Imaging Conditions
Collimator: LEPH pinhole collimator
Collecting Range: 360°
Step Angle: 11.25°
Collecting Time: 40 sec per direction
  1×32 frames per 60 sec (total: 32 min)
Reconfiguration Condition
Pretreatment Filter: Butterworth filter (order: 10, cutoff frequency: 0.08)

Figure 8:
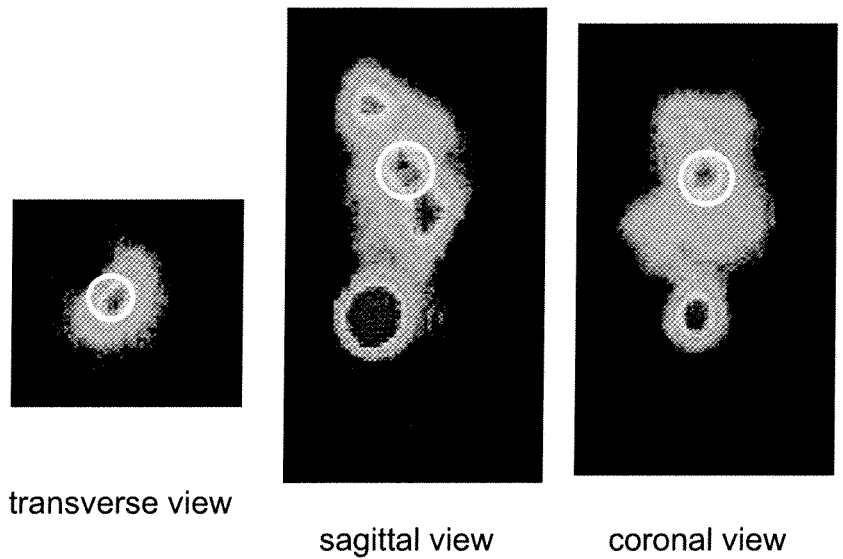
FIG. 8 is an exemplary SPECT image obtained using a molecular probe for imaging of Example 3.

Exemplary results are shown in FIG. 8. The images were taken at 30 minutes after the administration of the molecular probe (integrating time: 32 min). Shown in FIG. 8 are, starting from the left, a transverse view, a sagittal view and a coronal view. In FIG. 8, the positions of the pancreas are indicated by while circle.

As shown in FIG. 8, the position of the pancreas was confirmed noninvasively in mice with use of the molecular probe of the formula (13) above. In other words, it was confirmed that the molecular probe of the present invention enables the noninvasive three-dimensional imaging of the pancreas.

Thus, in view of that the position of the pancreas was confirmed noninvasively in a mouse that has the pancreas in a smaller size than that of a human and in which the organs are present more densely than in a human, this suggests that in a human that has the pancreas in a greater size than that of a mouse and in which the organs are present not as densely as in a mouse, the position of the pancreas and the size of the pancreas can be determined more clearly, and moreover, an amount of expression of the molecular probe in the pancreas can be determined.

These results suggest that the molecular probe for imaging according to the present invention enables noninvasive three-dimensional imaging of the pancreas, particularly noninvasive three-dimensional imaging of pancreatic β-cells and GLP-1R of the pancreatic β-cells, in a human.

INDUSTRIAL APPLICABILITY

As described above, the present invention is useful in, for example, the medical field, the molecular imaging field, and the field relating to diabetes.

SEQUENCE LISTING FREE TEXT

SEQ ID NO. 1: the amino acid sequence of the molecular probe for imaging of pancreatic islets according to the present invention SEQ ID NO. 2: the amino acid sequence of the precursor of molecular probe for imaging of pancreatic islets according to the present invention SEQ ID NO. 3: the amino acid sequence of the molecular probe for imaging of pancreatic islets of Example 1

SEQ ID NO. 4: the amino acid sequence of polypeptide used for producing a molecular probe for imaging of pancreatic islets of Example 1

SEQ ID NO. 5: the amino acid sequence of the molecular probe precursor used for producing the molecular probe for imaging of pancreatic islets of Example 1

SEQ ID NO. 6: the amino acid sequence of the molecular probe precursor of Reference Example 1

SEQ ID NO. 7: the amino acid sequence of the molecular probe of Reference Example 1

SEQ ID NO. 8: the amino acid sequence of the molecular probe precursor of Reference Example 2

SEQ ID NO. 9: the amino acid sequence of the molecular probe of Reference Example 2

SEQ ID NO. 10: the amino acid sequence of the molecular probe of Reference Example 3

SEQ ID NO. 11: the amino acid sequence of the molecular probe for imaging of Example 2

SEQ ID NO. 12: the amino acid sequence of the molecular probe of Reference Example 4

SEQ ID NO. 13: the amino acid sequence of the molecular probe for imaging of Example 3

SEQ ID NO. 14: the amino acid sequence of the polypeptide used in production of the molecular probe for imaging of the present invention.

SEQ ID NO. 15: the amino acid sequence of Exendin(9-39)

The invention claimed is:

1. A precursor of a molecular probe for imaging of pancreatic islets, the precursor being used for producing a molecular probe for imaging of pancreatic islets, the precursor comprising any one of the following polypeptides:
   a polypeptide represented by the following formula (2);
   a polypeptide obtained by deletion, insertion, or substitution of one to three amino acids with respect to the polypeptide represented by the following formula (2) and capable of binding to pancreatic islets after being labeled and deprotected; and
   a polypeptide having a homology of 95% or higher with the amino acid sequence of the polypeptide represented by the following formula (2) and capable of binding to pancreatic islets after being labeled and deprotected,

```
                                              (SEQ ID NO. 2)
*-HGEGTFTSDLSK*QMEEEAVRLFIEWLK*NGGPSSGAPPPSK-NH₂
```
(2)

wherein:
   "*-" indicates that an α-amino group at an N-terminus is protected by a protecting group, or is modified with a modifying group having no electric charge,
   "K*" indicates that an amino group of a side chain of a lysine is protected by a protecting group,
   "—NH₂" indicates that a carboxyl group at a C-terminus is amidated, and
   the functional groups of the side chains of the amino acids except for K* are not protected by a protecting group.

2. A method for producing a molecular probe for imaging of pancreatic islets, the method comprising:
   labeling and deprotecting the precursor of a molecular probe for imaging of pancreatic islets according to claim 1.

3. The method for producing a molecular probe for imaging of pancreatic islets according to claim 2,
   wherein the labeling of the precursor of a molecular probe for imaging of pancreatic islets includes labeling of the precursor with a compound having a group represented by the following chemical formula (I),

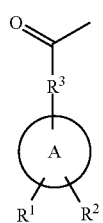

(I)

wherein:
   A represents an aromatic hydrocarbon group or an aromatic heterocyclic group, $R^1$ represents a substituent containing $^{11}C$, $^{13}N$, $^{15}O$, $^{18}F$, $^{75}Br$, $^{76}Br$, $^{77}Br$, $^{123}I$, $^{124}I$, $^{125}I$, or $^{131}I$, $R^2$ represents either a hydrogen atom, or one or more substituents different from that represented by $R^1$, and $R^3$ represents any one of a bond, an alkylene group having 1 to 6 carbon atoms, and an oxyalkylene group having 1 to 6 carbon atoms.

4. A method for imaging pancreatic islets, the method comprising
   producing a molecular probe for imaging of pancreatic islets by labeling and deprotecting the precursor of a molecular probe for imaging of pancreatic islets according to claim 1, and
   detecting a signal of the molecular probe for imaging of pancreatic islets, the molecular probe being preliminarily bound to the pancreatic islets.

5. The method for imaging pancreatic islets according to claim 4, the method further comprising determining a state of pancreatic islets on the basis of results of the imaging of pancreatic islets using the molecular probe for imaging of pancreatic islets.

6. A method for determining an amount of pancreatic islets, the method comprising:
   detecting a signal of the molecular probe for imaging of pancreatic islets obtained by the method according to claim 2, the molecular probe being preliminarily bound to pancreatic islets; and
   calculating an amount of pancreatic islets from the detected signal of the molecular probe for imaging of pancreatic islets.

7. The method for determining an amount of pancreatic islets according to claim 6, further comprising presenting the calculated amount of pancreatic islets.

8. The precursor according to claim 1, where in the formula (2), "K" indicates that an amino group of a side chain of a lysine is not modified.

9. The precursor according to claim 1, wherein the precursor comprises the polypeptide represented by the formula (2).

10. The precursor according to claim 1, wherein the precursor consists of the polypeptide represented by the formula (2).

11. The precursor according to claim 1, wherein the precursor comprises the polypeptide obtained by deletion, insertion, or substitution of one amino acid with respect to the polypeptide represented by the formula (2).

12. The precursor according to claim 1, wherein the precursor comprises the polypeptide obtained by deletion, insertion, or substitution of two amino acids with respect to the polypeptide represented by the formula (2).

13. The precursor according to claim 1, wherein the precursor comprises the polypeptide having a homology of 95% or higher with the amino acid sequence of the polypeptide represented by the formula (2).

14. A kit for imaging of pancreatic islets, the kit comprising a precursor of a molecular probe comprising any one of the following polypeptides:
- a polypeptide represented by the following formula (2);
- a polypeptide obtained by deletion, insertion, or substitution of one to several amino acids with respect to the polypeptide represented by the following formula (2) and capable of binding to pancreatic islets after being labeled and deprotected; and
- a polypeptide having a homology of 80% or higher with the amino acid sequence of the polypeptide represented by the following formula (2) and capable of binding to pancreatic islets after being labeled and deprotected, (SEQ ID NO. 2)
\*-HGEGTFTSDLSK\*QMEEEAVRLFIEWLK\*NGGPSSGAPPPSK-NH$_2$ (2)

wherein:
- "\*-" indicates that an α-amino group at an N-terminus is protected by a protecting group, or is modified with a modifying group having no electric charge,
- "K\*" indicates that an amino group of a side chain of a lysine is protected by a protecting group, and
- "—NH$_2$" indicates that a carboxyl group at a C-terminus is amidated.

15. The kit according to claim 14, wherein the precursor of the molecular probe included in the kit is in a form of a parenteral solution.

\* \* \* \* \*

SEQUENCE LISTING

<160> NUMBER OF SEQ ID NOS: 15

<210> SEQ ID NO 1
<211> LENGTH: 40

```
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group.
<220> FEATURE:
<221> NAME/KEY: MOD_RES
<222> LOCATION: (40)..(40)
<223> OTHER INFORMATION: An amino group of a side chain is labeled.
      A carboxyl group of a C-terminus is amidated.

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 2
<211> LENGTH: 40
<212> TYPE: PRT
<213> ORGANISM: Artificial Sequence
<220> FEATURE:
<223> OTHER INFORMATION: A precursor of a molecular probe for imaging
      of pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group.
<220> FEATURE:
<221> NAME/KEY: MOD_RES
<222> LOCATION: (12)..(12)
<223> OTHER INFORMATION: An amino group of a side chain is protected
      by a protecting group.
<220> FEATURE:
<221> NAME/KEY: MOD_RES
<222> LOCATION: (27)..(27)
<223> OTHER INFORMATION: An amino group of a side chain is protected
      by a protecting group.
<220> FEATURE:
<221> NAME/KEY: MOD_RES
<222> LOCATION: (40)..(40)
<223> OTHER INFORMATION: A carboxyl group of a C-terminus is amidated.

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 3
<211> LENGTH: 40
<212> TYPE: PRT
<213> ORGANISM: Artificial Sequence
<220> FEATURE:
<223> OTHER INFORMATION: A molecular probe for imaging of pancreatic
      islets of Example 1
<220> FEATURE:
<221> NAME/KEY: MOD_RES
<222> LOCATION: (40)..(40)
<223> OTHER INFORMATION: An amino group of a side chain is labeled by
```

[18F]fluorobenzoyl. A carboxyl group of a C-terminus is amidated.

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 4
<211> LENGTH: 40
<212> TYPE: PRT
<213> ORGANISM: Artificial Sequence
<220> FEATURE:
<223> OTHER INFORMATION: A polypeptide for preparation of precursor of
      a molecular probe for imaging of pancreatic islets of Example 1
<220> FEATURE:
<221> NAME/KEY: MOD_RES
<222> LOCATION: (1)..(1)
<223> OTHER INFORMATION: An alpha-amino group of an N-terminus is
      protected by a Fmoc.  A functional group of a side chain is
      protected by a Trt.
<220> FEATURE:
<221> NAME/KEY: MOD_RES
<222> LOCATION: (3)..(3)
<223> OTHER INFORMATION: A functional group of a side chain is protected
      by a OBu.
<220> FEATURE:
<221> NAME/KEY: MOD_RES
<222> LOCATION: (8)..(8)
<223> OTHER INFORMATION: A functional group of a side chain is protected
      by a OBu.
<220> FEATURE:
<221> NAME/KEY: MOD_RES
<222> LOCATION: (9)..(9)
<223> OTHER INFORMATION: A functional group of a side chain is protected
      by a OBu.
<220> FEATURE:
<221> NAME/KEY: MOD_RES
<222> LOCATION: (11)..(11)
<223> OTHER INFORMATION: A functional group of a side chain is protected
      by a OBu.
<220> FEATURE:
<221> NAME/KEY: MOD_RES
<222> LOCATION: (12)..(12)
<223> OTHER INFORMATION: An amino group of a side chain is protected by
      a Mmt.
<220> FEATURE:
<221> NAME/KEY: MOD_RES
<222> LOCATION: (13)..(13)
<223> OTHER INFORMATION: A functional group of a side chain is protected
      by a Trt.
<220> FEATURE:
<221> NAME/KEY: MOD_RES
<222> LOCATION: (15)..(17)
<223> OTHER INFORMATION: A functional group of a side chain is protected
      by a OBu.
<220> FEATURE:
<221> NAME/KEY: MOD_RES
<222> LOCATION: (20)..(20)
<223> OTHER INFORMATION: A functional group of a side chain is protected
      by a Pdf.
<220> FEATURE:
<221> NAME/KEY: MOD_RES
<222> LOCATION: (24)..(24)
<223> OTHER INFORMATION: A functional group of a side chain is protected
      by a OBu.
<220> FEATURE:
<221> NAME/KEY: MOD_RES
<222> LOCATION: (25)..(25)
<223> OTHER INFORMATION: A functional group of a side chain is protected
      by a Boc.
<220> FEATURE:
<221> NAME/KEY: MOD_RES

```
<222> LOCATION: (27)..(27)
<223> OTHER INFORMATION: An amino group of a side chain is protected by
      a Mmt.
<220> FEATURE:
<221> NAME/KEY: MOD_RES
<222> LOCATION: (28)..(28)
<223> OTHER INFORMATION: A functional group of a side chain is protected
      by a Trt.
<220> FEATURE:
<221> NAME/KEY: MOD_RES
<222> LOCATION: (32)..(33)
<223> OTHER INFORMATION: A functional group of a side chain is protected
      by a OBu.
<220> FEATURE:
<221> NAME/KEY: MOD_RES
<222> LOCATION: (39)..(39)
<223> OTHER INFORMATION: A functional group of a side chain is protected
      by a OBu.
<220> FEATURE:
<221> NAME/KEY: MOD_RES
<222> LOCATION: (40)..(40)
<223> OTHER INFORMATION: An amino group of a side chain is protected by
      a Boc.

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 5
<211> LENGTH: 40
<212> TYPE: PRT
<213> ORGANISM: Artificial Sequence
<220> FEATURE:
<223> OTHER INFORMATION: A precursor of a molecular probe for imaging of
      pancreatic islets of Example 1
<220> FEATURE:
<221> NAME/KEY: MOD_RES
<222> LOCATION: (1)..(1)
<223> OTHER INFORMATION: An amino group of an N-terminus is protected by
      a Fmoc
<220> FEATURE:
<221> NAME/KEY: MOD_RES
<222> LOCATION: (12)..(12)
<223> OTHER INFORMATION: An amino group of a side chain is protected by
      a Fmoc.
<220> FEATURE:
<221> NAME/KEY: MOD_RES
<222> LOCATION: (27)..(27)
<223> OTHER INFORMATION: An amino group of a side chain is protected by
      a Fmoc.
<220> FEATURE:
<221> NAME/KEY: MOD_RES
<222> LOCATION: (40)..(40)
<223> OTHER INFORMATION: A carboxyl group of a C-terminus is amidated.

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 6
<211> LENGTH: 31
<212> TYPE: PRT
<213> ORGANISM: Artificial Sequence
```

```
<220> FEATURE:
<223> OTHER INFORMATION: A precursor of a molecular probe of reference
      example 1
<220> FEATURE:
<221> NAME/KEY: MOD_RES
<222> LOCATION: (1)..(1)
<223> OTHER INFORMATION: An amino group of an N-terminus is protected
      by a Fmoc.
<220> FEATURE:
<221> NAME/KEY: MOD_RES
<222> LOCATION: (19)..(19)
<223> OTHER INFORMATION: An amino group of a side chain is protected by
      a Fmoc.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 6

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: A molecular probe of reference example 1
<220> FEATURE:
<221> NAME/KEY: MOD_RES
<222> LOCATION: (4)..(4)
<223> OTHER INFORMATION: An amino group of a side chain is labeled by
      [18]fluorobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 7

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: A precursor of a molecular probe of reference
      example 2
<220> FEATURE:
<221> NAME/KEY: MOD_RES
<222> LOCATION: (1)..(1)
<223> OTHER INFORMATION: An amino group of an N-terminus is protected
      by a Fmoc.
<220> FEATURE:
<221> NAME/KEY: MOD_RES
<222> LOCATION: (4)..(4)
<223> OTHER INFORMATION: An amino group of a side chain is protected by
      a Fmoc.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 8

Asp Leu Ser Lys Gln Met Glu Glu Glu Ala Val Arg Leu Phe Ile Glu
1               5                   10                  15
```

```
Trp Leu Lys Asn Gly Gly Pro Ser Ser Gly Ala Pro Pro Pro Ser
            20                  25                  30
```

<210> SEQ ID NO 9
<211> LENGTH: 31
<212> TYPE: PRT
<213> ORGANISM: Artificial Sequence
<220> FEATURE:
<223> OTHER INFORMATION: A molecular probe of reference example 2
<220> FEATURE:
<221> NAME/KEY: MOD_RES
<222> LOCATION: (19)..(19)
<223> OTHER INFORMATION: An amino group of a side chain is labeled by
      [18]fluorobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 9

```
Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30
```

<210> SEQ ID NO 10
<211> LENGTH: 32
<212> TYPE: PRT
<213> ORGANISM: Artificial Sequence
<220> FEATURE:
<223> OTHER INFORMATION: A molecular probe of reference example 3
<220> FEATURE:
<221> NAME/KEY: MOD_RES
<222> LOCATION: (32)..(32)
<223> OTHER INFORMATION: An amino group of a side chain is labeled by
      [18F]fluorobenzoyl. A carboxyl group of a C-terminus is amidated.

<400> SEQUENCE: 10

```
Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser Lys
            20                  25                  30
```

<210> SEQ ID NO 11
<211> LENGTH: 40
<212> TYPE: PRT
<213> ORGANISM: Artificial Sequence
<220> FEATURE:
<223> OTHER INFORMATION: A molecular probe for imaging of pancreatic
      islets of Example 2
<220> FEATURE:
<221> NAME/KEY: MOD_RES
<222> LOCATION: (40)..(40)
<223> OTHER INFORMATION: An amino group of a side chain is labeled by
      [125I]3-iodobenzoyl. A carboxyl group of a C-terminus is amidated.

<400> SEQUENCE: 11

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40
```

<210> SEQ ID NO 12
<211> LENGTH: 32
<212> TYPE: PRT
<213> ORGANISM: Artificial Sequence

```
<220> FEATURE:
<223> OTHER INFORMATION: A molecular probe of reference example 4
<220> FEATURE:
<221> NAME/KEY: MOD_RES
<222> LOCATION: (32)..(32)
<223> OTHER INFORMATION: An amino group of a side chain is labeled by
      [125I]3-iodobenzoyl. A carboxyl group of a C-terminus is amidated.

<400> SEQUENCE: 12

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser Lys
            20                  25                  30

<210> SEQ ID NO 13
<211> LENGTH: 40
<212> TYPE: PRT
<213> ORGANISM: Artificial Sequence
<220> FEATURE:
<223> OTHER INFORMATION: A molecular probe for imaging of pancreatic
      islets of Example 3
<220> FEATURE:
<221> NAME/KEY: MOD_RES
<222> LOCATION: (40)..(40)
<223> OTHER INFORMATION: An amino group of a side chain is labeled by
      [123I]3-iodobenzoyl. A carboxyl group of a C-terminus is amidated.

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 14
<211> LENGTH: 40
<212> TYPE: PRT
<213> ORGANISM: Artificial Sequence
<220> FEATURE:
<223> OTHER INFORMATION: A polypeptide for use in preparation of
      labelled polypeptide

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys
        35                  40

<210> SEQ ID NO 15
<211> LENGTH: 31
<212> TYPE: PRT
<213> ORGANISM: Artificial Sequence
<220> FEATURE:
<223> OTHER INFORMATION: Exendin-(9-39)
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 15
```

```
Asp Leu Ser Lys Gln Met Glu Glu Glu Ala Val Arg Leu Phe Ile Glu
1               5                   10                  15
Trp Leu Lys Asn Gly Gly Pro Ser Ser Gly Ala Pro Pro Pro Ser
            20                  25                  30
```